United States Patent
Nicolson

(10) Patent No.: US 12,338,471 B2
(45) Date of Patent: *Jun. 24, 2025

(54) USE OF GLUTAMINE SYNTHETASE FOR TREATING HYPERAMMONEMIA

(71) Applicant: Thoeris GmbH, Vienna (AT)

(72) Inventor: Tamara Nicolson, London (GB)

(73) Assignee: Thoeris GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 17/832,564

(22) Filed: Jun. 3, 2022

(65) Prior Publication Data

US 2022/0401532 A1 Dec. 22, 2022

Related U.S. Application Data

(62) Division of application No. 16/616,884, filed as application No. PCT/GB2018/051415 on May 24, 2018.

(30) Foreign Application Priority Data

May 24, 2017 (GB) .................................... 1708288
Jan. 19, 2018 (GB) .................................... 1800867

(51) Int. Cl.
| | |
|---|---|
| *C12N 9/00* | (2006.01) |
| *A61K 31/216* | (2006.01) |
| *A61K 38/43* | (2006.01) |
| *A61K 38/53* | (2006.01) |
| *A61K 47/60* | (2017.01) |
| *A61P 3/00* | (2006.01) |
| *A61P 7/00* | (2006.01) |
| *C07K 14/00* | (2006.01) |
| *C07K 19/00* | (2006.01) |

(52) U.S. Cl.
CPC ........ *C12N 9/93* (2013.01); *C12Y 603/01002* (2013.01); *A61K 31/216* (2013.01); *A61K 38/43* (2013.01); *A61K 38/53* (2013.01); *A61K 47/60* (2017.08); *A61P 3/00* (2018.01); *A61P 7/00* (2018.01); *C07K 14/00* (2013.01); *C07K 19/00* (2013.01)

(58) Field of Classification Search
CPC ....................................................... C12N 9/93
See application file for complete search history.

(56) References Cited

U.S. PATENT DOCUMENTS

| | | |
|---|---|---|
| 6,812,339 B1 | 11/2004 | Venter et al. |
| 7,590,493 B2 | 9/2009 | Mendrick et al. |
| 7,745,391 B2 | 6/2010 | Mintz et al. |
| 2002/0160425 A1 | 10/2002 | Jackowski et al. |
| 2003/0144357 A1 | 7/2003 | Brusilow et al. |
| 2007/0083334 A1 | 4/2007 | Mintz et al. |
| 2009/0209474 A1 | 8/2009 | Roegel et al. |
| 2009/0280124 A1 | 11/2009 | Labat et al. |

FOREIGN PATENT DOCUMENTS

| | | | |
|---|---|---|---|
| CN | 109504709 A | 3/2019 | |
| CN | 110714057 A | 1/2020 | |
| EP | 1381866 B1 | 6/2004 | |
| EP | 3966332 A0 | 11/2020 | |
| JP | 2003225093 A | 8/2003 | |
| JP | 2003274963 A | 9/2003 | |
| JP | 2004527754 | 9/2004 | |
| JP | 2007525997 | 9/2007 | |
| JP | 2013529911 | 7/2013 | |
| MX | 2014013566 A | 5/2016 | |
| RU | 2362572 C2 | 7/2009 | |
| WO | 2002088706 A2 | 11/2002 | |
| WO | 2003029461 A1 | 4/2003 | |
| WO | 2004060270 A2 | 7/2004 | |
| WO | 2004106489 A2 | 12/2004 | |
| WO | 2005019258 A2 | 3/2005 | |
| WO | 2007071339 A1 | 6/2007 | |
| WO | 2010026443 A1 | 3/2010 | |
| WO | WO-2013020914 A1 * | 2/2013 | ....... A61K 47/48215 |
| WO | 2013137583 A1 | 9/2013 | |
| WO | 2013186371 A1 | 12/2013 | |
| WO | 2016085887 A1 | 6/2016 | |
| WO | 2017173043 A1 | 10/2017 | |
| WO | 2017197098 A1 | 11/2017 | |
| WO | 2018093331 A1 | 5/2018 | |
| WO | 2019014652 A1 | 1/2019 | |

(Continued)

OTHER PUBLICATIONS

Fransceus. J Ind Microbiol Biotechnol. May 2017;44(4-5):687-695.*
Sanavia. Computational and Structural Biotechnology Journal, vol. 18, 2020, pp. 1968-1979.*
Gibbs. Sequence of a human glutamine synthetase cDNA. Nucleic Acids Res. 15:6293-6293 (1987).*
Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Reichel Stohry Dean LLP; Natalie J. Dean

(57) ABSTRACT

The present invention relates to the use of glutamine synthetase as a protein therapy (such as enzyme replacement protein therapy) for the treatment of hyperammonemia. In particular the invention relates to the systemic administration of glutamine synthetase. The glutamine synthetase may be provided in conjugated or fusion form, to increase its half-life in the circulation. Also provided is a pharmaceutical composition comprising glutamine synthetase. The invention also relates to the uses, methods, and compositions involving a combination of the glutamine synthetase protein and an ammonia lowering agent, such as a nitrogen scavenger.

17 Claims, 10 Drawing Sheets
Specification includes a Sequence Listing.

(56) References Cited

FOREIGN PATENT DOCUMENTS

| WO | 2019028273 A1 | 2/2019 |
| WO | 2019129215 A1 | 4/2019 |

OTHER PUBLICATIONS

GLNA_HUMAN. UnitProtKB/Swiss-Prot Database. May 11, 2016.*
Spriestersbach. Purification of His-Tagged Proteins. Methods Enzymol. 2015;559:1-15. Epub May 4, 2015.*
Chen. Fusion protein linkers: property, design and functionality. Adv Drug Deliv Rev. Oct. 2013;65(10):1357-69. Epub Sep. 29, 2012.*
Patent Translate Powered by EPO and Google English Translation of RU2362572, Description RU2362572C2 in English, last visited Jun. 13, 2022, DE.
Google.com/patents English Translation of CN109504709, The albumin expression vectors of albumin promoter driving, last visited Aug. 17, 2022, US.
Patent Translate Powered by EPO and Google English Translation of CN110714057A, Description CN110714057A in English, last visited Jun. 10, 2022, DE.
Patent Translate Powered by EPO and Google English Translation of JP2003274963, Description JP2003274963A in English, last visited Jun. 10, 2022, DE.
Patent Translate Powered by EPO and Google English Translation of JP2003225093A, Marker for Cartilage Disorder and Use Thereof in English, last visited Sep. 28, 2022, DE.
Google.com/patents English Translation of MX2014013566, Gene therapy to treat hyperammonemia in hepatic encephalopathy and other liver diseases, last visited Aug. 17, 2022, US.
Albrecht and Norenberg, Glutamine: A Trojan Horse in Ammonia Neurotoxicity, Hepatology 44(4): 788-794 (2006), American Association for the Study of Liver Diseases, US.
Krajewsky et al., Crystal Structures of Mammalian Glutamine Synthetases Substrate-Induced Conformational Changes and Provide Opportunities for Drug and Herbicide Design, J Mol Biol 375: 217-228 (2008), Elsevier, NL.
Listrom et al., Expression, Purification, and Characterization of Recombinant Human Glutamine Synthetase, Biochem J 328: 159-163 (1997), American Chemical Society, US.
Wang et al., Production of Glutamine Synthetase in *Escherichia Coli* Using SUMO Fusion Partner and Application to L-Glutamine Synthesis, World J Microbiology Biotech 27: 2603-2610 (2011), Springer Science + Business Media, DE.
Shin and Park, N-Terminal Extension of Canine Glutamine Synthetase Created by Splicing Alters Its Enzymatic Property, J Biological Chem 279(2): 1184-1190 (2004), American Society for Biochemistry and Molecular Biology, US.
Haberle et al., Congenital Glutamine Deficiency with Glutamine Synthetase Mutations, N Engl J Med 353(18): 1926-1933 (Nov. 3, 2005), Massachusetts Medical Society, US.
Frieg et al., Determining the Molecular Consequences of Clinically Relevant Glutamine Synthetase, Zeitschrift für Gastroenterologie 53(12), DOI:10.1055/s-0035-1567974 (2015), Thieme Medical Publishers, DE.
Freig et al., Molecular Mechanisms of Glutamine Synthetase Mutations that Lead to Clinically Relevant Pathologies, PloS Computational Bio 12(2): e1004693 (Feb. 2006), PLOS, US.
Spodenkiewicz et al., Minireview on Glutamine Synthetase Deficiency, an Ultra-Rare Inborn Error of Amino Acid Biosynthesis, Biology 5(4): 40 (Oct. 19, 2016), MDPI, CH.
Kosenko et al., Encapsulation of Glutamine Synthetase in Mouse Erythrocytes: A New Procedure for Ammonia Detoxification, Biochem Cell Bio 86(6): 469-476 (Dec. 2008), Elsevier, NL.
Braissant et al., Ammonia Toxicity to the Brain, J Inheritable Metabolic Disease 36(4): 595-612 (2013), Springer Science + Business Media, DE.
Rose, Ammonia-Lowering Strategies for the Treatment of Hepatic Encephalopathy, Clinical Pharm & Therapeutics 92 (3): 321-331 (2012), Wiley-Blackwell, US.
Duarte-Rojo et al., Changes in Peripheral Blood Mononuclear Cells Glutamine Synthetase mRNA After Exercise in Healthy Volunteers: Exploring an Alternative Proposal for Non Hepatic Ammonia Metabolism, Revista de Investigacion Clinica 64(2):164-72 (2012), National Institutes of Health of Mexico, MX.
Jover-Cobos et al., Muscle Glutamine Synthase Regulates the Severity of Hyperammonemia, Hepatic Inflammation, Brian Swelling and Survival in Acetaminophen Hepatotoxicity, J Hepatology 58: S218-S219 (2013), Elsevier, NL.
Keda, PEGylation Technology for the Drug Development, Drug Delivery System 31(4): 268-274 (2016), The Japan Society of Drug Delivery System, JP.
Torres-Vega et al., Delivery of Glutamine Synthese Gene by Baculovirus Vectors: A Proof of Concept for the Treatment of Acute Hyperammonemia, Gene Therapy 22: 58-64 (2015), Springer Nature, DE.
Haberle, Clinical and Biochemical Aspects of Primary and Secondary Hyperammonemic Disorders, Archives Biochem & Biophysics 536(2):101-8 (Aug. 15, 2013); doi0.1016/j.abb.2013.04.009 (Epub Apr. 27, 2013), Elsevier, NL.
Matoori and Leroux, Recent Advances in the Treatment of Hyperammonemia, Adv Drug Delivery Rev 90: 55-68 (2015), Elsevier, NL.
Hakvoort et al., Pivotal Role of Glutamine Synthetase in Ammonia Detoxification, Hepatology 65(1): 281-293 (2017), Elsevier, NL.
International Searching Authority, International Search Report, PCT Application Serial No. PCT/GB2018051415, dated Aug. 15, 2018.
International Searching Authority, Written Opinion of the International Searching Authority, PCT Application Serial No. PCT/GB2018051415, dated Aug. 15, 2018.
Torres-Vega et al., "Delivery of glutamine synthetase gene by baculovirus vectors: a proof of concept for the treatment of acute hyperammonemia," Gene Therapy, Oct. 23, 2014, 22(1): 58-64, Macmillan Publishers Limited, GB.
Nao et al., Vancouver General Hospital CSU Pharmaceutical Sciences Special Access Program (SAP) Drug Data Sheet Drug Name Sodium Phenylacetate / Sodium Benzoate (SA/SB), Vancouver General Hospital, Jul. 2007, CA.
Torres-Vega et al., "Reduction of hyperammonemia in vitro and in vivo by a baculovirus-delivered glutamine synthetase as a new approach for the treatment of hepatic encephalopathy," Molecular Therapy, 21(S1): S231, May 1, 2013, The American Society of Gene & Cell Therapy, US.
Sharma et al., "Review Article: Next Generation Delivery System for Proteins and Genes of Therapeutic Purpose: Why and How?", BioMed Research Internat'l, vol. 2014, Article ID 327950, Jul. 15, 2014, pp. 1-11, Hindawi Publishing Company, UK.
Shin et al., N-terminal extension of canine glutamine synthetase created by splicing alters its enzymatic property, J of Biological Chemistry 279(2): 1184-1190 (2004), US.
Emergency Management in Neurocritical Care 158 (Edward Manno ed., Wiley) (2012), US.
Hilsabeck & Webb, Hepatic Encephalopathy, in Handbook on the Neuropsychology of Aging and Dementia, Chapter 29: 467-485 (Lisa D. Ravdin & Heather L. Katzen eds., Springer Publishing) (2013), US.
Platt & Garosi, Small Animal Neurological Emergencies 488 (2012), Manson Publishing Limited, UK.
Inborn Errors of Metabolism, Chapter 6: 139 (Brendan Lee ed., Oxford University Press) (2014), UK.
Albecht et al., Brain Glutamine Roles in Norm and Pathology, in Glutamine Biochemistry, Physiology and Clinical Applications, Chapter 7: 97-110 (Dominique Meynial-Denis ed., CRC Press) (2017), US.
Morgan et al., The Treatment of Hepatic Encephalopathy, Metabolic Brain Disease 22: 389-405 (2007), Springer Publishing, US.
Patel et al., Clinical Science Workshop: Targeting the Gut-Liver-Brain Axis, Metabolic Brain Disease 31: 1327-1337 (2016), Springer Publishing, US.
Hepatic Encephalopathy 9 (Mullen & Prakash eds., Springer Publishing) (2012), US.

(56) References Cited

OTHER PUBLICATIONS

Curthoys, Glutaminase Isoforms and Glutamine Metabolism, in Glutamine Biochemistry, Physiology and Clinical Applications, Chapter 3: 31-42 (Dominique Meynial-Denis ed., CRC Press) (2017), US.

Mpabanzi et al., To Pee or Not to Pee: Ammonia Hypothesis of Hepatic Encephalopathy Revisited, European J of Gastroenterology & Hepatology 23: 449-454 (2011), Lippincott Williams & Wilkins, US.

Deuel et al., Glutamine Synthetase from Rat Liver. Purification, Properties, and Preparation of Specific Antisera, J Biological Chemistry, 253(17): 6111-6118 (1978).

\* cited by examiner

USE OF GLUTAMINE SYNTHETASE FOR TREATING HYPERAMMONEMIA

PRIORITY

The present application is a divisional application of, related to, and claims the priority benefit of, U.S. application Ser. No. 16/616,884, filed Nov. 25, 2019, which is related to, claims the priority benefit of, and is a 35 U.S.C. 371 national stage application of International Patent Application No. PCT/GB2018/051415, filed May 24, 2018, which is related to, and claims the priority benefit of: (a) Great Britain Patent Application Serial No. 1708288.4, filed May 24, 2017; and (b) Great Britain Patent Application Serial No. 1800867.2, filed Jan. 19, 2018. The contents of the aforementioned applications are hereby incorporated by reference in their entireties into this disclosure.

TECHNICAL FIELD

The present invention relates to the use of glutamine synthetase as a protein therapy (such as enzyme replacement protein therapy) for the treatment of hyperammonemia, and in particular to the systemic administration of glutamine synthetase. The glutamine synthetase is thus administered as a protein, or polypeptide, with the aim of increasing circulating levels of glutamine synthetase. The glutamine synthetase may be provided in conjugated or fusion form, to increase its half-life in the circulation. Also provided is a pharmaceutical composition comprising glutamine synthetase. The invention also relates to the uses, methods and compositions involving a combination of the glutamine synthetase protein and an ammonia lowering agent, such as a nitrogen scavenger.

BACKGROUND

Hyperammonemia is a metabolic condition characterised by increased, or excess, ammonia in the blood. It is a dangerous condition, principally since it may lead to increased entry of ammonia to the brain, which in turn causes neurological disorders and neuropsychiatric abnormalities, which can be very severe, leading to, inter alia, brain damage, seizures, retardation, coma and even death. Indeed, encephalopathy is a common and hazardous complication of hyperammonemia. Although precise mechanisms for encephalopathy/brain damage are not yet understood, astrocytic osmotic stress caused by the increased ammonia is believed to play a role, leading to cerebral oedema and increased intracranial pressure. Hyperammonemia may be congenital or acquired, and may be primary or secondary.

Primary (congenital) hyperammonemia arises from various inborn errors of metabolism characterised by reduced activity of any of the enzymes or transporter proteins of the urea cycle. Indeed, such inborn errors of metabolism form a group of diseases called urea cycle disorders (UCD). Ammonia ($NH_3$), which may co-exist in the body with its charged form ammonium ($NH_4^+$) depending on pH, is a product of the catabolism of proteins and other nitrogenous compounds. It is converted by the enzymes of the urea cycle to the less toxic substance urea prior to excretion in urine by the kidneys. The urea cycle, which also functions as the sole source of production of certain amino acids (arginine, citrulline and ornithine) in the body, comprises 6 enzymes, the five catalytic enzymes carbamoyl phosphate synthetase I (CPS1), ornithinetranscarbamylase (OTC), or argininosuccinic acid synthetase (ASS1), arginosuccinic acid lyase (ASL) and arginase (ARG), and the co-factor producing enzyme N-acetylglutamate synthetase (NAGS) and 2 transporter proteins ornithine translocase (ORNT1) and citrin. A defect can occur in any one or more of these 8 proteins. Severe deficiency or total absence of activity of any of the first four enzymes or of NAGS result in accumulation of ammonia and other precursor metabolites during the first few days of life. Infants with a severe UCD are normal at birth but rapidly develop cerebral oedema and the related signs of lethargy, anorexia, hyper- or hypoventilation, hyperthermia, seizures, neurologic posturing and coma. Severity of the UCD is influenced by the position of the defective enzyme in the pathway and severity of the enzyme defect. With rapid identification and current treatment strategies, survival of neonates with hyperammonemia has improved dramatically in the last few decades, but intellectual ability is typically impaired. In milder, or partial, deficiencies of these enzymes and in ARG deficiency ammonia accumulation may be triggered by illness or stress at almost any time of life. In these disorders the elevations of plasma ammonia concentration and symptoms are often more subtle than the neonatal presentation of a UCD, and the first recognised clinical episode may not occur for months or decades.

Secondary hyperammonemia is caused by inborn errors of intermediary metabolism characterised by reduced activity in enzymes/proteins that are not part of the urea cycle, e.g. propionic acidaemia, methyl malonic acidaemia, galactosaemia, fatty acid oxidation disorders and mitochondrial disorders, or by dysfunction of cells (e.g. the liver) that make major contributions to ammonia metabolism and/or nitrogen metabolism more generally.

Acquired hyperammonemia is usually caused by liver diseases, including both acute and chronic liver failure, such as viral hepatitis or excessive alcohol consumption. Impaired liver function or vascular bypass of the liver, resulting in decreased filtration of blood in the liver, leads to hyperammonemia. Hepatic encephalopathy due to hyperammonemia is a common complication of liver disease.

Hyperammonemia may also occur for other reasons including renal dysfunction e.g. kidney dysfunction and/or failure, drug toxicity e.g. due to valproic acid or cyclophosphamide, idiopathic hyperammonemia syndrome after immunosuppression or cytotoxic therapy, ureolysis in stagnant urine and urinary tract infections, or essential amino acid total parenteral nutrition.

Current treatments for hyperammonemia are designed to reduce ammonia levels in the blood and/or the brain e.g. by haemodialysis (typically used in neonates) or by administering compounds that increase removal of nitrogen waste, for example non-absorbable disaccharides (e.g. lactulose) or antibiotics (e.g. rifaxamin) or compounds that convert nitrogen into products other than urea which are then excreted, e.g. compounds such as sodium benzoate, arginine, carglumic acid, phenylacetate or more latterly phenylbutyrate, or L-ornithine L-aspartate (LOLA) or L-ornithine phenylacetate (OP).

Management of the condition may also include dietary control to restrict protein intake and ensure adequate nutritional intake, including management of protein and/or nitrogen intake and parenteral intake of calories.

However, despite improvements in treatment and management of the condition current therapies are non-specific and do not always succeed in managing the condition successfully. In the case of UCD particularly, current therapies may not prevent many elevated ammonia events and patients with severe forms of the disease are often assessed for liver transplant around age 5. There is therefore a continuing need for further or improved therapies for hyperammonemia.

BRIEF SUMMARY

The present invention seeks to address this need and is based on the concept of using glutamine synthetase to detoxify ammonia by converting it to the non-toxic product glutamine. In particular, the present invention proposes systemically to administer glutamine synthetase as a protein therapy to reduce the levels of ammonia in the blood.

Glutamine synthetase (GS) catalyses the reaction:

Glutamate+ATP+NH$_3$→Glutamine+ADP+phosphate.

Glutamine synthesis occurs in a number of organs of the body and may play a role in organ and whole-body nitrogen balance. Very recently, gene therapy based on overexpression of GS in the skeletal muscle has been proposed for the treatment of acute hyperammonemia (Torres-Vega et al, Gene Therapy 2015, 22, 58-64), the rationale for this therapy being to replace or augment GS which is generally deficient in the muscles of patients with liver disease, thereby aiming to increase the clearance of ammonia by this enzyme in the muscle. Gene therapy has however proved difficult to successfully administer in clinical practice and not all patients are suitable for it (e.g. children, with the exception of stem-cell based gene therapies), or patients may be refractory to gene therapy (e.g. for immune reasons). Further, such a therapy would produce a mainly localised effect, in the muscle. Accordingly, a need still remains for a more generally applicable therapy.

Administration of GS systemically as a protein may serve to achieve such a more general effect. We have shown that GS, particularly human GS, may successfully be expressed and purified and may retain, or demonstrate, GS activity, both in unmodified and modified form, conjugated to a polymeric partner such as polyethylene glycol. Further, animal studies have shown that high circulating levels of the GS may be achieved by systemic administration and that both modified and unmodified GS administered to the animal retains activity in the blood and other tissues (e.g. liver). Thus, therapeutic levels of GS may be achieved by systemic (e.g. parenteral) administration of GS protein.

Additionally, the inventors have also surprisingly found that the combined use of a GS protein and an ammonia lowering agent (such as a nitrogen scavenger, for example, a pharmaceutically acceptable salt of phenylacetic acid, such as sodium phenylacetate) has a synergistic effect and may further increase the ability of the GS protein to treat or prevent hyperammonemia. Accordingly, in one aspect the present invention provides a glutamine synthetase (GS) protein for use in treating or preventing hyperammonemia by systemic non-oral administration to a subject.

In a suitable embodiment, the GS protein for use in treating of preventing hyperammonemia, may be for use in combination with an ammonia lowering agent.

In another aspect, the invention provides an ammonia lowering agent for use in combination with a GS protein, for use in treating or preventing hyperammonemia.

A related aspect of the invention also provides use of a GS protein for the manufacture of a composition (e.g. a pharmaceutical or nutritional composition, for example a medicament or supplement) for the treatment or prevention of hyperammonemia by systemic non-oral administration to a subject.

In a suitable embodiment, the composition may be for use in combination with an ammonia lowering agent.

A further aspect of the invention also provides use of an ammonia lowering agent for the manufacture of a composition for use in combination with a GS protein for the treatment or prevention of hyperammonemia.

In a further aspect the present invention provides use of a GS protein and an ammonia lowering agent for the manufacture of a composition for use in the treatment or prevention of hyperammonemia.

In a further aspect the present invention provides a method of treating or preventing hyperammonemia in a subject, said method comprising systemically and non-orally administering a GS protein to a said subject (more particularly to a subject in need thereof). In a suitable embodiment, the method further comprises administering an ammonia lowering agent.

Also provided is a composition comprising a GS protein, for use in treating or preventing hyperammonemia by systemic non-oral administration to a subject.

Suitably, the composition comprising a GS protein may be a pharmaceutical or nutritional composition, for example a medicament or supplement. Suitably, the composition may further comprise an ammonia lowering agent.

The invention also relates to a composition comprising an ammonia lowering agent, for use in treating or preventing hyperammonemia. Suitably, the composition comprising an ammonia lowering agent may be a pharmaceutical or nutritional composition, for example a medicament or supplement.

The invention also relates to a composition comprising a GS protein and an ammonia lowering agent.

Suitably the composition may be a pharmaceutical or nutritional composition. Suitably, the composition may be for use in treating or preventing hyperammonemia.

DETAILED DESCRIPTION

The term "GS protein" may alternatively be expressed as "a protein having glutamine synthetase (GS) activity". The term "protein" is used broadly used herein to include any proteinaceous molecule, including peptides and polypeptides, as well as protein or polypeptide fragments; the GS protein does not have to be, or to correspond to, a full length GS enzyme as it appears in nature (e.g. a native or wild-type GS) and truncated or other variants are included, as described more detail below. Also included are conjugates, or fusions, of the GS protein with other molecules, as also described in more detail below.

The term "hyperammonemia" includes any condition in which ammonia in the blood (or as measured or determined in any blood-derived product or sample e.g. blood plasma) is elevated as compared to the level of ammonia in a subject without the condition, e.g. a healthy subject or a subject without the underlying condition which leads to or causes the hyperammonemia. In health, ammonia transport and metabolism are tightly regulated to maintain a low plasma/blood concentration (normal range 10-40 μmol/L). Thus, a plasma (or blood) ammonia concentration of >40, 60 or 70 or 80 μmol/L or more, e.g. 41, 42, 45, 50, 55, 60, 70 or 80 μmol/L or more may be viewed as indicative of hyperammonemia. For example, a plasma ammonia concentration of >100 μmol/L, and particularly 150 μmol/L or higher, where associated with a normal anion gap and a normal plasma glucose concentration, may be indicative of hyperammonemia, or more particularly, indicate the presence of a UCD.

Hyperammonemia may arise from any of the causes or conditions discussed above, i.e. it may be congenital or acquired, primary or secondary, as discussed above. Thus, in one embodiment the hyperammonemia may arise due to (or be associated with) a urea cycle disorder (UCD). As discussed above, the UCD may arise from a defect in any one or more of the proteins of the urea cycle, which may inactivate or reduce the activity of the protein.

In a further embodiment the hyperammonemia may arise due to an inborn error of metabolism affecting a protein (e.g. enzyme) which is not part of the urea cycle, but which affects nitrogen metabolism and/or balance in the body, and leads to an increase in the amount of ammonia in the blood. Suitably, such an inborn error of metabolism may be glutamine synthetase deficiency.

In still further embodiments, the hyperammonemia may be acquired and may arise to disease or damage to an organ or tissue of the body which is involved in nitrogen metabolism and/or balance, for example in catabolism and/or excretion of nitrogen-containing molecules or substances e.g. the liver or kidney.

Thus any kind of liver damage or disease, including both chronic or acute liver failure, for example liver damage due to excess alcohol consumption or due to drugs (whether recreational or medicinal), cirrhosis of the liver due to any cause, non-alcoholic fatty liver disease, infection of the liver or trauma to the liver may lead to hyperammonemia.

Similarly, any kind of damage to or disease of the kidney is described for the liver above may also lead to hyperammonemia. Thus, any condition affecting multiple organs of the body (e.g. multiple organ failure) such as for example sepsis, organ damage from injury (whether external injury e.g. trauma, or internal injury e.g. from autoimmune disorders), or any systemic infection, may give rise to hyperammonemia.

Hyperammonemia may be detected or diagnosed based on clinical, biochemical and/or molecular genetic data, depending upon the underlying cause. Thus for example it may be detected by assessing or monitoring blood levels of ammonia (e.g. in plasma or serum or any blood-derived sample) according to techniques well known and used in the art. Analysis of amino acids present in the blood (plasma or serum, etc.) and/or the concentration thereof (for example arginine or citrulline) or other metabolites in the blood or other body fluids or tissues (e.g. orotic acid in urine) may also help to identify that a UCD is involved, and/or will determine the precise nature thereof (i.e. the specific protein/enzyme defect involved). Such determinations and analyses may be combined with clinical assessments, e.g. neurological and neuropsychiatric evaluations, including both physical (e.g. MRI or other imaging) and/or behavioural/response tests etc., liver and/or kidney or other organ function tests etc. In the case of a suspected UCD, investigations of family history and/or molecular genetic tests and/or assessments of enzyme activity of the urea cycle enzymes may also be undertaken.

As used herein, reference to a glutamine synthetase or GS protein for use according to the present invention includes reference to all forms of enzymatically-active GS, including human GS and GS from non-human animals (such as mouse, cow, rabbit, rat, monkey, chimpanzee, and dog etc), or from other sources including for example fungi, plants or bacteria, as well as enzymatically-active variants. Representative GS proteins thus include those having at least 50%, 55%, 60%, 65%, 70%, 75%, 80%, 85%, 90%, 91%, 92%, 93%, 94%, 95%, 96%, 97%, 98%, 99% or more sequence identity with the GS polypeptide set forth in SEQ ID NO: 1 or 2 or 4 (human GS, precursor, mature and N-terminal tagged forms respectively) or with the GS polypeptide set forth in SEQ ID NO: 6 (GS from *Lactobacillus acididophilus* strain 30SC) or SEQ ID NO: 7 (GS from corn, *Zea Mays*), or an enzymatically-active fragment thereof. For example, reference to GS may also include N- and/or C-terminally truncated polypeptides or amino acid modified protein (eg. post-translational modifications, such as adenylation, or other modifications such as amino acid polymorphisms that may affect the structure or activity of the protein). It may also include multimers of the protein. The term "GS" thus includes all native forms of GS enzymes or polypeptides as well as enzymatically-active fragments or variants thereof, including synthetically derived and modified polypeptides having one or more amino acid substitutions, additions (including insertions and extensions) or deletions, which retain GS enzymatic activity.

The GS may thus be, or may be derived from, any enzyme falling within the enzyme classification EC 6.3.1.2. It may be any polypeptide or peptide having GS activity. GS activity may be defined as the ability to convert glutamate and ammonia to glutamine, e.g. according to the reaction scheme set out above. GS activity may be assessed or determined using assays or tests (e.g. a functional activity assay) as known in the art and described in the literature. For example, GS enzyme activity assays are described in Listrom et al, Biochem. J. 1997, 328, 159-163. An assay for GS activity is also described in the Examples below (see Examples 2 and 4).

The term also includes a pro-drug for the GS, that is a form which does not in itself exhibit GS activity, but which may be converted to an active GS upon administration to the subject.

Thus, as used herein, "enzymatically-active" with reference to a GS protein or polypeptide refers to a GS protein or polypeptide that can catalyze the conversion of glutamate and ammonia to glutamine. Typically, the enzymatically-active GS protein or polypeptide exhibits at least or about 30%, 40%, 50%, 60%, 70%, 80%, 90%, 95%, 96%, 97%, 98% or 99% of the enzymatic activity of a GS polypeptide as set forth in SEQ ID NO:1, 2, 4, 6 or 7.

The term "subject" as used herein includes any human or non-human animal and particularly refers to mammals, including for example humans, primates, livestock animals (e.g. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal. Even more preferably, the mammal is a human.

As used herein the terms "treating", "treatment", "preventing" and "prevention" refer to any and all uses which remedy or ameliorate a condition or symptoms, prevent the establishment of a condition or disease, or otherwise prevent, hinder, retard, reduce or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery, but includes any improvement or amelioration in the condition of a patient or subject, or in a symptom of the disease or condition. Thus for example in the case of a UCD, treatment according to the present invention does not of course treat the underlying genetic disorder, but rather the resulting clinical condition of hyperammonemia. In conditions which display or are characterized by multiple symptoms, the treatment or prevention need not necessarily remedy, ameliorate, prevent, hinder, retard, reduce or reverse all of said symptoms, but may remedy, ameliorate, prevent, hinder, retard, reduce or reverse one or more of said symptoms. In a suitable embodiment, "treatment" according to the present invention a reduction in the levels of ammonia in the blood, to for example normal or healthy levels, e.g. to the range 10-40 µmol/L. Thus, treatment includes the restoration of normal or healthy ammonia levels. Similarly, prevention according to the present invention may include maintenance of plasma/blood ammonia levels in any normal or healthy range, as indicated above.

In a suitable embodiment, "treatment" according to the present invention may include an increase in glutamine synthetase levels and/or activity in subject's tissue, to for example normal or healthy levels. Such an increase may be in any suitable tissue (for example liver and/or muscle). An increase in glutamine synthetase levels and/or activity may be, for example, determined by measuring levels of glutamine, levels of glutamate, and/or determining the ration between levels of glutamine and levels of glutamate, in a subject. It will be appreciated that normal or healthy levels of glutamine and/or glutamate may vary depending on the sample in which these are measured. It will also be appreciated that normal or healthy levels of glutamine and/or glutamate may be subject specific, and depend on factors such as the subject's weight, diet, sex and age. Normal or healthy levels of glutamine and/or glutamate will be known to those skilled in the art.

In a suitable embodiment "treatment" according to the present invention may include a reduction in oedema. The term "oedema" as used herein refers to abnormal accumulation of serous fluid in the subject. In a suitable embodiment, oedema may be brain oedema, pulmonary oedema, peripheral oedema, and/or macular oedema. Suitably, in the context of the present invention, "treatment" may refer to a reduction in brain oedema, for example in the prefrontal cortex. By way of example, oedema may be assessed by a CT scan, MRI, and/or an x-ray. Other methods of assessing oedema will be known to those skilled in the art.

In a suitable embodiment "treatment" according to the present invention may include an improvement in neuropsychological, neuropsychiatric and neurocognitive function. The term "neuropsychological, neuropsychiatric and neurocognitive function" refers to the function of the brain which controls, for example, memory, attention, cognition, psychomotor activity, coordination and mood. Uses, methods and compositions of the invention which involve the combination of a GS protein and an ammonia lowering agent may be particularly useful in such an embodiment. Various methods for assessing neural function will be known to those skilled in the art. The neuronal functional status may be assessed using electroencephalography, computerised tests, paper and pencil tests and assessments by a neuropsychologist.

In a suitable embodiment "treatment" according to the present invention may include an improvement in sarcopenia and physical function. The term "sarcopenia" refers to reduced muscle mass. The term "physical function" refers to the subject's strength, in particular muscle strength. The severity of sarcopenia may be determined by using clinical tools, nutritional tools, measurement of body composition or imaging. Physical function may be assessed, for example, by assessment of oxygen delivery and consumption, exercise test and hand-grip test, and/or an improvement in levels of fatigue, and/or immune system function.

As used herein, "amelioration" refers to the lessening of severity of at least one indicator or symptom of a condition or disease. In certain embodiments, amelioration includes a delay or slowing in the progression of one or more indicators of a condition or disease. The severity of indicators may be determined by subjective or objective measures, which are known to those skilled in the art.

As used herein the term "associated with" when used in the context of a disease or condition "associated with" the elevated levels of ammonia means that the disease or condition may result from, result in, be characterised by, or otherwise associated with the elevated levels of ammonia. Thus, the association between the disease or condition and the elevated levels of ammonia may be direct or indirect and may be temporally separated.

Appropriate samples for determination of levels of ammonia include any appropriate or desired sample in which the ammonia may occur. By the same token, appropriate samples for determination of glutamine synthetase levels and/or glutamine synthetase activity, include any appropriate or desired sample in which glutamine synthetase, glutamine and/or glutamate may be present. These may be any appropriate or desired tissue or body fluid sample. An example of a suitable tissue is liver and/or muscle tissue. Conveniently, a sample may be any body fluid sample, and typically will be blood or any blood-derived sample e.g. plasma or serum etc, but it may be any other body fluid e.g. urine, cerebrospinal fluid, or a stool or tissue sample etc, for example a biopsy sample or a lavage or washing fluid sample etc. This may depend of course on the precise nature of the condition to be treated etc.

As used herein the term "effective amount" includes within its meaning a non-toxic but sufficient amount or dose of, depending on the context, GS protein and/or an ammonia lowering agent, to provide the desired effect. It will be appreciated that the effective amount of the protein and/or the ammonia lowering agent may be different. Exemplary therapeutically effective amounts are specified elsewhere in this specification.

The exact amount or dose required will vary from subject to subject depending on factors such as the species being treated, the age and general condition of the subject, the severity of the condition being treated, the particular FMO3 being administered and the mode of administration and so forth. Thus, it is not appropriate to specify an exact "effective amount". However, for any given case, an appropriate "effective amount" may be determined by one of ordinary skill in the art using only routine experimentation.

Human GS is expressed as a polypeptide of 373 amino acids (as shown in SEQ ID NO: 1). This represents the full "precursor" protein as expressed which is then further processed to a mature form having amino acids 2-373 (only the N-terminal methionine is removed to yield a mature protein of 372 amino acids in vivo, as shown in SEQ ID NO: 2. The exemplary polynucleotide set forth in SEQ ID NO:3 represents a cDNA encoding the polypeptide of SEQ ID NO: 1. SEQ ID NO: 4 represents a modified human GS protein, comprising the GS polypeptide of SEQ ID NO: 1 provided with an N-terminal His-tag and linker sequence, as prepared and used in the Examples below. SEQ ID NO: 5 is a cDNA sequence encoding the polypeptide of SEQ ID NO: 4, codon-optimised for expression in bacteria, as used in the Examples below.

Human GS has been well-characterised (see for example Listrom et al., 1997, supra). GS enzymes from other organisms, including plants and bacteria, have also been identified, and nucleic acid and amino acid sequences of such other GS enzymes are well known in the art and provided in freely-available databases, such as, for example, the National Center for Biotechnology Information (NCBI) Nucleotide (ncbi.nlm.nih.gov/nuccore) and Protein (ncbi.nlm.nih.gov/protein) databases. Although the sequence identity between plant or bacterial GS enzymes and human GS may be low, the structural and functional similarity is high. Accordingly, plant or bacterial GS, or indeed GS from other organisms, or amino acid sequence variants thereof, may be used. By way of representative example, SEQ ID NO:6 sets forth the amino acid sequence of the GS from *Lactobacillus acidophilus* strain 30SC, which has 23.8% sequence identity with human GS and 61.9% sequence identity with the GS of *Lactobacillus casei*, and SEQ ID NO: 7 sets forth the amino acid sequence of the GS from corn (maize, *Zea Mays*), which has 55.7% sequence identity with human GS.

GS commonly occurs as a multimer comprising multiple (i.e. 2 or more) monomer subunits. The GS amino acid sequence provided above, for example, represents such a monomer subunit. Human GS is most frequently reported as a dodecamer (12 subunits). As used herein, the GS may be provided as a monomer and/or as a multimer. The multimer may comprise 2 or more monomer subunits, for example 2 to 20, 2 to 16, 2 to 15, 2 to 14 or 2 to 12 subunits.

Indeed, a surprising feature of the present invention is that contrary to the reports in the literature of a 12-subunit multimer, human GS may be expressed and/or obtained as a mixture of multiple different types of multimer, including also a monomeric form. The monomeric form has been shown to be active. Thus, according to the present invention, the GS may be used as a monomer and/or as a multimer, and the multimer may be provided as a single multimeric form, or as a mixture of different multimeric forms which may or may not include the monomer. As reported in the examples below, 4 or more, e.g. 4 to 10, e.g. 5 to 8 multimeric forms may be obtained. The multimers may range in size from 2 to 20 subunits.

The GS protein used in the methods provided herein can be obtained by any method known in art, such as recombinant methods, protein isolation and purification methods and chemical synthesis methods, providing the resulting GS exhibits enzymatic activity. Accordingly, the GS can be recombinant GS, native GS isolated from tissue, or chemically synthesised GS.

It is well within the capabilities of a skilled person to modify a GS polypeptide, such as the polypeptide set forth in SEQ ID NO:1, to generate enzymatically-active GS variants for use in the methods provided herein. For example, a person skilled in the art would understand that modifications at positions involved in substrate binding, or in the active site, are less likely to be tolerated than modifications at positions outside these critical regions. Any GS polypeptide can be tested using methods well known in the art, such as those described in the Examples below, to assess the ability of the GS polypeptide to catalyze the conversion of glutamate and ammonia to glutamine.

In some examples, the GS used according to the invention herein is recombinant GS produced using prokaryotic or eukaryotic expression systems well known in the art. Exemplary prokaryotic expression systems include, but are not limited to, *Escherichia coli* expression systems, and exemplary eukaryotic expression systems include, but are not limited to, yeast, insect cell and mammalian cell expression systems.

Nucleic acid encoding GS can be obtained by any suitable method, including, but not limited to, RT-PCR of liver RNA and synthetic nucleotide synthesis. Primers for amplification can be designed based on known GS sequences, such as that set forth above. Nucleic acid and amino acid sequences of GS are well known in the art and provided in freely-available databases, such as, for example, the National Center for Biotechnology Information (NCBI) Nucleotide (ncbi.nlm.nih.gov/nuccore) and Protein (ncbi.nlm.nih.gov/protein) databases.

Nucleic acid encoding the GS polypeptide, such as nucleic acid having a sequence set forth in SEQ ID NO:3, can be cloned into an expression vector suitable for the expression system of choice. In some instances, the nucleic acid is codon-optimized for expression in a particular system. For example, the nucleic acid encoding the GS polypeptide can be codon-optimised for expression in *E. coli*. An exemplary codon-optimised nucleic acid encoding GS for expression in *E. coli* is set forth in SEQ ID NO 5, which encodes a GS polypeptide comprising a His-tag attached via a GGGGS linker (as set forth in SEQ ID NO:4).

Typically the nucleic acid encoding the GS is cloned into an expression vector, operably linked to regulatory sequences that facilitate expression of the heterologous nucleic acid molecule. Many expression vectors suitable for the expression of GS are available and known to those of skill in the art. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

GS polypeptides also can be expressed as protein fusions. For example, a fusion can be generated to add additional functionality to a polypeptide. Examples of fusion proteins include, but are not limited to, fusions containing GS and an affinity tag for purification (e.g. a his-tag e.g. his6, MYC, FLAG, HA or GST tag), a leader sequence (such as the pelB leader sequence), a sequence for directing protein secretion, or a protein for stabilising and/or solubilising GS (e.g. maltose-binding protein (MBP)), or a protein for increasing in vivo half-life (e.g. albumin or Fc domains, or fragments thereof).

Prokaryotes, especially *E. coli*, provide a system for producing large amounts of GS. Transformation of *E. coli* is a simple and rapid technique well known to those of skill in the art. Expression vectors for *E. coli* can contain inducible promoters that are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated APL promoter.

In other examples, eukaryotic expression systems are used to produce the GS, such as baculovirus expression systems. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda*, *Pseudaletia unipuncta* (A7S) and *Danaus plexippus* (DpNl). For high level expression, the nucleotide sequence of the GS is fused immediately downstream of the polyhedrin initiation codon of the virus.

Yeasts such as *Saccharomyces cerevisiae, Schizosaccharomyces pombe, Yarrowia lipolytica, Kluyveromyces lactis,* and *Pichia pastoris* can also be used expression hosts for GS. Yeast can be transformed with episomal replicating vectors or by stable chromosomal integration by homologous recombination. Typically, inducible promoters, such as include GAL1, GAL7, and GAL5, are used to regulate gene expression. Yeast expression vectors often include a selectable marker such as LEU2, TRP1, HIS3, and URA3 for selection and maintenance of the transformed DNA.

Mammalian expression systems also can be used to express GS. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). Exemplary cell lines available for mammalian expression include, but are not limited to, mouse, rat, human, monkey, and chicken and hamster cells, such as BHK, 293-F, CHO, Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells.

Following expression, GS can be purified using any method known to those of skill in the art including, but not limited to, SDS-PAGE, size fraction and size exclusion chromatography, ammonium sulfate precipitation, chelate chromatography, ionic exchange chromatography and affinity chromatography. Affinity purification techniques can be used to improve the efficiency and purity of the preparations. For example, antibodies and other molecules that bind GS can be used in affinity purification. As discussed above, expression constructs can be engineered to add an affinity tag such as a his, myc, FLAG or HA tag or GST moiety to GS, which can then be affinity purified with Ni-resin, myc antibody, HA antibody, FLAG antibody or glutathione resin, respectively. Purity can be assessed by any method known in the art including gel electrophoresis and staining and spectrophotometric techniques, such as SDS page and Size Exclusion Chromatography (SEC).

For use according to the present invention, the affinity tag (e.g. his tag etc) may be removed, but this is not necessary, and the GS polypeptide may be used with the tag attached.

The tag or other fusion partner may be attached to the GS via a linker, which may be any suitable linker, according to principles well known in the art. Such a linker may typically and conveniently be a short (e.g. 2 to 10, 2 to 8 or 2-6 mer) peptide. By way of example the linker GGSG may be mentioned, but could be made up of any suitable amino acids. Amino acid linkers enable preparation of the fusion protein by recombinant means but non-amino acid-based linkers might also be used, again according to principles and techniques well known in the art and described in the literature. The linker may be cleavable (e.g. enzymatically) or non-cleavable.

GS polypeptides can be prepared as naked polypeptide chains or as modified polypeptides which are modified by coupling or conjugating to a further moiety or chemical group or substance. Exemplary modifications include, but are not limited to, pegylation, albumination or other known modifications. For example, in some instances, the GS polypeptides for use in the described methods are peglyated using standard methods well known in the art. This may serve, for example, to improve the half-life of the GS protein in the circulation. Thus, in a preferred embodiment of the invention the GS protein may be provided as a conjugate with a polymer such as polyethylene glycol (PEG) or a poly- or oligosaccharide. Conjugates with PEG are particularly preferred. As indicated above the preparation of such conjugates is well known in the art and described in the literature. Thus, PEGs of various sizes may be used to prepare the conjugates e.g. ranging from 100 Daltons to 100 kD, but more often from 5 kD to 100 kD, for example 12 or 15 kD to 60 or 80 kD, such as 15 to 50, 15 to 40, or 15 to 30 kD. Further, the PEG may be attached or linked to the GS protein in various ways, and more than one PEG may be attached to each single protein. It may be linked directly or indirectly, e.g. via a linker as described, for fusion proteins above or by any molecular or chemical group which may provide a linker function. Thus, the PEG may be linked at one or both of the N- or C-termini, or internally in the GS molecule, for example at the amino group of one or more lysine residues in the GS protein molecule or at any other chemical moiety or residue in the protein molecule. Methods for coupling or conjugating polymers such as PEG to proteins are well known in the art and described in the literature (see for example Roberts et al. 2012, Advanced Drug Delivery Reviews, 64 (supplement) 116-127 and Veronese 2001, Biomaterials 22, 405-417). The data presented in the Examples below shows that PEG conjugates prepared by linking the PEG to the N-terminal are especially effective, for example in activity assays of liver lysates from animals administered various conjugates. Accordingly, a PEG conjugate comprising a PEG linked to the N terminus of a GS protein represents one preferred embodiment of the present invention. The GS protein may be pegylated in monomeric and/or multimeric form. Thus, for convenience a preparation comprising both monomeric and various multimeric forms of GS may be subjected to pegylation.

GS can be formulated as a pharmaceutical composition for administration to a subject. GS can be formulated in any conventional manner by mixing a selected amount of GS with one or more physiologically or pharmaceutically acceptable carriers or excipients.

Accordingly, a further aspect of the invention provides a pharmaceutical composition comprising a GS protein and one or more pharmaceutically-acceptable carriers or excipients, wherein the composition is for non-oral systemic administration.

Selection of the carrier or excipient is within the skill of the administering profession and can depend upon a number of parameters, such as the mode of administration. In some examples the GS is provided as a fluid. In other instances, the GS is provided in dried form, such as desiccated or freeze-dried form. Such dried forms can be rehydrated prior to administration by the addition of a suitable solution, such as water, buffer, saline or other suitable solution. The GS provided herein can be formulated for direct administration or can be formulated for dilution or other modification. Accordingly, the GS can be formulated in single (or unit) dosage forms or multiple dosage forms. Examples of single dose forms include ampoules and syringes. Examples of multiple dose forms include vials and bottles that contain multiple unit doses.

The concentrations of the GS in the formulations are effective for delivery of an amount of GS that, upon administration, is effective to convert ammonia to glutamine in the presence of glutamate. The concentrations and amounts will depend on several factors, including the levels of the substrates in the subject, and mode of administration, and can be empirically determined. Exemplary concentrations of GS in the compositions provided herein include, but are not limited to, concentrations of or about 0.1, 0.5, 0.6, 0.7, 0.8, 0.9, 1, 5, 10, 15, 20, 30, 40, 50, 60, 70, 80, 90, 100, 200, 300, 400, 500, 1000, 2000, 3000, 4000 or 5000 mg/mL GS or more.

To formulate the GS composition, in one embodiment the weight fraction of GS is dissolved, suspended, dispersed, or otherwise mixed in a selected vehicle at the desired concentration. The resulting mixtures are solutions, suspensions, emulsions and other such mixtures, and can be formulated as a non-aqueous or aqueous mixture, including but not limited to, a solution, suspension, paste, gel, aerosol, spray, or any other formulation suitable for systemic administration.

Generally, the GS composition is prepared in view of approval from a regulatory agency or otherwise prepared in accordance with generally recognized pharmacopeia for use in animals and in humans. The GS composition can include carriers such as a diluent, excipient, or vehicle. Such pharmaceutical carriers can be sterile liquids, such as water and oils. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A GS composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents. Examples of suitable pharmaceutical carriers are described in "Remington's Pharmaceutical Sciences" by E. W. Martin.

Liposomal suspensions, including tissue-targeted liposomes, can also be suitable as pharmaceutically acceptable carriers. These can be prepared according to methods known to those skilled in the art. Liposomal delivery can also include slow release formulations, including pharmaceutical matrices such as collagen gels and liposomes modified with fibronectin.

As well as in pharmaceutical compositions, the GS may also be formulated or administered in other ways, for example in a nutritional composition such as a dietary supplement, for example a parenteral nutrition composition (e.g. alone or alongside other supplement ingredients). It may be included in such foods as a polypeptide (e.g. purified enzyme) or as part of an expressing host cell or organism. Thus for example microbial (e.g. yeast or bacterial or fungal) host cells or plants (including plants cells) may be engineered to express GS and may be administered as such, e.g. a whole cells or extracts or other processed products (in which enzymatic activity may be retained), or may be incorporated into nutritional compositions. Thus, for example, bacterial or yeast cells suitable for human or non-human animal consumption may be engineered to express GS (namely by introduction of a nucleic acid molecule comprising a nucleotide sequence encoding GS). Alternatively, plants may be engineered in an analagous manner and appropriate plant parts etc (e.g. seeds, leaves, tubers etc) may be provided for administration. It is known in the art which microorganisms (yeasts, bacteria, algae or fungi for example) are suitable for human or other animal consumption and many such organisms are used today, for example in probiotic formulations. Any such probiotic organisms or formulations could be used e.g. based on lactic acid bacteria such as *Bifidobacterium* or *Lactobacillus* sp. (e.g. *L. acidophilus*) etc. Thus, according to the present invention such organisms or preparations may be formulated for and administered directly into the GI tract, e.g. by injection or infusion, or enema or rectal administration etc.

The precise amount or dose of the GS administered to the subject depends on the activity of the GS, the route of administration, the disease or condition being treated, the number of dosages administered, and other considerations, such as the weight, age and general state of the subject. Particular dosages and administration protocols can be empirically determined or extrapolated from, for example, studies in animal models. Exemplary therapeutically effective doses of the GS include, but are not limited to, from or from about 0.1 µg/kg body weight per day to or to about 10000 µg/kg body weight per day, including from or from about 1 µg/kg to or to about 1000 µg/kg body weight per day, or from or from about 10 µg/kg to or to about 100 µg/kg body weight per day Thus, for example, a subject can be administered 0.1, 0.2, 0.3, 0.4, 0.5, 1, 5, 10, 20, 30, 40, 50, 60, 70, 80, 90, 100, 200, 400, 600, 800, 1000, 2000, 4000, 6000, 8000, 10000, or 20000 µg or more the GS per kg body weight per day.

It is a feature of the present invention that the GS is administered systemically, but non-orally. By "orally" it is meant per-oral delivery. Accordingly, non-oral means that the GS protein is not administered by ingestion via the mouth. Although other means of administration which deliver the GS protein to the intestines or more generally the gastrointestinal (GI) tract may be included (e.g rectally, or by enema, or direct administration into the GI tract), in certain embodiments they are excluded. Accordingly, in a certain embodiment the invention includes enteral administration, but in another embodiment it does not. In a further embodiment the invention does not include administration to the muscle, particularly to skeletal muscle. Thus, in such an embodiment the administration is not directed to muscle, i.e. is a non-muscle directed therapy.

Accordingly the GS can be administered by any method and route that delivers the GS protein systemically to the body, but does not involve oral administration. In certain embodiments the GS protein may be administered parenterally. A skilled artisan would readily understand and be able to select appropriate modes of administration or delivery, including, but not limited to, intravenous, intramuscular, intradermal, transdermal, subcutaneous, or intraperitoneal administration, as well as by any combination of any two or more thereof, formulated in a manner suitable for each route of administration. In some instances, the GS compositions described herein are administered subcutaneously. In other instances the GS compositions may be administered intravenously. For example, the GS compositions can be administered intravenously by injection or infusion, such as by an intravenous bolus.

The GS protein may also be administered in conjunction or combination with other therapeutic or active agents, notably a second or further therapeutic agent which may treat (e.g. to improve) hyperammonemia. A second or further therapeutic agent which is active to treat hyperammonemia may be alternatively defined as an anti-hyperammonemia agent or as an agent against hyperammonemia. The second or further agent may typically be an ammonia lowering agent such as a nitrogen scavenger (or an ammonia scavenger) or a replacement amino acid or urea cycle intermediate, or an analogue thereof. Such an agent may therefore include an amino acid, for example arginine, glutamate, citrulline and/or ornithine, and/or N-acetyl glutamate and/or the analogue molecule carbamyl glutamate (Carbaglu®). More suitably, the second or further agent is an ammonia lowering agent, more suitably a nitrogen scavenger. Such an embodiment gives rise to certain aspects of the present invention.

The term "ammonia lowering agent" refers to a compound which removes ammonia and/or reduces, or inhibits ammonia production. An ammonia lowering agent may be selected from the group consisting of a nitrogen scavenger, an ion exchange resin (for example Relapsa), an ammonia absorber (such a liposomal based ammonia absorber, for example Versantis), an engineered microbiome that removes ammonia (for example Synlogic), Rifaximin and Lactulose.

The term "nitrogen scavenger" as used herein, refers to a compound which reduces the levels of nitrogen and/or ammonia in a subject by removing ammonia. In a suitable embodiment the nitrogen scavenger reduces the amount of nitrogen and/or ammonia in the subject by being metabolised to phenylacetyl glutamine, which may be then excreted in urine.

In a suitable embodiment, a nitrogen scavenger may be selected from the group consisting of a pharmaceutically acceptable salt of phenylacetic acid (also referred to herein as phenylacetate), a pharmaceutically acceptable salt of phenylbutyric acid (also referred to herein as phenylbutyrate), glycerol phenylbutyrate, a pharmaceutically acceptable salt of benzoic acid, a pharmaceutically acceptable pro-drug thereof, and ammonia binding resin. Other nitrogen scavengers will be well known to those skilled in the art.

As used herein, the term "pharmaceutically-acceptable salt" includes, for example, an acid-addition salt of phenylacetic acid which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of phenylacetic acid which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl) amine.

In a suitable embodiment, a pharmaceutically acceptable salt of phenylacetic acid may be selected from the group consisting of sodium phenylacetate, potassium phenylacetate, ornithine phenylacetate.

In a suitable embodiment, a pharmaceutically acceptable salt of phenylbutyric acid may be selected from the group consisting of sodium phenylbutyrate and potassium phenylacetate.

In a suitable embodiment, a pharmaceutically acceptable salt of benzoic acid may be selected from the group consisting of sodium benzoate and potassium benzoate.

It shall be understood that an ammonia lowering agent may exist in solvated as well as unsolvated forms such as, for example, hydrated forms. It is to be understood that in the context of the present invention encompassed are all such solvated and unsolvated forms.

The term "pro-drug" as used herein refers to an agent rendered less active by a chemical or biological moiety than the ammonia lowering agent (such as nitrogen scavenger), but which metabolises into or undergoes in vivo hydrolysis to form the ammonia lowering agent.

In particular, agents such as phenylacetate or phenylbutyrate compounds are preferred, which act to remove glutamine from the circulation (glutamine being formed by the action of GS). The second or further agent, such as an ammonia lowering agent, may be administered separately, sequentially or simultaneously with the GS protein, including in the same formulation or composition, or in a separate composition or formulation.

Accordingly, in a further aspect, the invention provides a product comprising a GS protein for systemic non-oral administration and a further therapeutic agent, as a combined preparation for separate, simultaneous or sequential use in treating or preventing hyperammonemia.

The second or further agent may be administered by the same administration route or by a different administration route, including orally. Thus, in one exemplary embodiment the second or further, such as an ammonia lowering agent, agent may be administered orally, or by other systemic means and the GS may be administered by non-oral systemic means.

Ammonia lowering agents, such as nitrogen scavengers (including sodium phenylacetate, ornithine phenylacetate, sodium phenyl butyrate, or sodium benzoate) may be administered by intravenous infusion e.g. for acute management, and/or orally, e.g for long-term maintenance. The i.v. infusion may be peripheral but central i.v. infusion is preferred. Similarly amino acids such as arginine may be administered orally or i.v., for example by central i.v. infusion.

Accordingly, a yet further aspect of the present invention provides a product (e.g. a combination product) comprising a GS protein for systemic non-oral administration and a further therapeutic agent as a combined preparation for separate, simultaneous or sequential use in treating or preventing hyperammonemia. In a suitable embodiment, such a further therapeutic agent may be an ammonia lowering agent. More suitably the ammonia lowering agent may be a nitrogen scavenger. More suitably, the nitrogen scavenger may be a pharmaceutically acceptable salt of phenylacetic acid, more suitably sodium phenylacetate.

Alternatively viewed, this aspect of the invention also provides a kit comprising (a) a GS protein for systemic non-oral administration and (b) a further therapeutic agent. Suitably, the further therapeutic may be effective against hyperammonemia. Suitably, the further therapeutic agent is an ammonia lowering agent, more suitably a nitrogen scavenger.

Accordingly, in a further aspect the invention provides a kit comprising (a) a GS protein for systemic non-oral administration and (b) a nitrogen scavenger. Suitably, the nitrogen scavenger may be a pharmaceutically acceptable salt of phenylacetic acid, more suitably sodium phenylacetate.

Such kits may be provided for use in treating or preventing hyperammonemia. The components of the kit may be provided as separate pharmaceutical compositions comprising the agent(s) in question together with one or more pharmaceutically-acceptable carriers or excipients. The composition(s) of the invention can be administered once or more than once. If the composition(s) are administered more than one time, they can be administered at regular intervals or as needed, for example as determined by a clinician. Regular intervals can include, for example, approximately daily, weekly, bi-weekly, monthly, or any other interval. Selecting a treatment protocol is well within the level of skill of the skilled artisan. For example, a protocol can be determined based upon studies in animal models. In other example, repeat doses of the composition(s) can be administered to a subject if the ammonia level in the blood, is above a predetermined level.

The use of the GS protein, or the use of the ammonia lowering agent in combination with a GS protein, according to the present invention is advantageous for the treatment of subjects for whom gene therapy is not suitable or appropriate, for example children or subjects who are refractory to gene therapy. Such refractory subjects may include for example those who have previously been exposed to, or have had an immune reaction to, the viral vector used for delivery of the gene therapy.

Advantageously, the use of a protein as the therapeutic agent allows higher doses of the active protein to be delivered to the subject and for doses to be adjusted according to subject and to need. Furthermore, as compared to gene therapy, protein therapy allows for a much faster response, and hence is more suitable for emergency use.

As mentioned, one aspect of the invention relates to a pharmaceutical composition comprising an ammonia lowering agent, for use in combination with GS protein for use in treating or preventing hyperammonemia. The ammonia lowering agent can be formulated as a pharmaceutical composition for administration to a subject. The ammonia lowering agent, can be formulated in any conventional manner by mixing a selected amount of the nitrogen scavenger, with one or more physiologically or pharmaceutically acceptable carriers or excipients. Suitably, the composition may be for non-oral systemic administration, or oral administration. It will be appreciated that the pharmaceutical composition may also comprise GS protein. In such an embodiment, the composition will be formulated for non-oral systemic administration.

Selection of the carrier or excipient is within the skill of the administering profession and can depend upon a number of parameters, such as the mode of administration. In some examples the ammonia lowering agent, is provided as a fluid. In other instances, the ammonia lowering agent, is provided in dried form. Such a dried form can be rehydrated prior to administration by the addition of a suitable solution, such as water, buffer, saline or other suitable solution. The ammonia lowering agent can be formulated for direct administration or can be formulated for dilution or other modification. Accordingly, the ammonia lowering agent can be formulated in single (or unit) dosage forms or multiple dosage forms. Examples of single dose forms include ampoules and syringes. Examples of multiple dose forms include vials and bottles that contain multiple unit doses.

The concentrations of the ammonia lowering agent in the formulations are effective for delivery of an amount of ammonia lowering agent that, upon administration, is effective to remove nitrogen and/or ammonium from the circulation, or reduce or inhibit ammonia production. The concentrations and amounts will depend on several factors, including the levels of the substrates in the subject, and mode of administration, and can be empirically determined. Exemplary concentrations of the ammonia lowering agent in the compositions provided herein include, but are not limited to, concentrations of or about 0.1, 0.5, 0.6, 0.7, 0.8, 0.9, 1, 5, 10, 15, 20, 30, 40, 50, 60, 70, 80, 90, 100, 200, 300, 400, 500, 1000, 2000, 3000, 4000 or 5000 mg/mL of ammonia lowering agent or more.

To formulate the ammonia lowering agent composition, in one embodiment the weight fraction the ammonia lowering agent is dissolved, suspended, dispersed, or otherwise mixed in a selected vehicle at the desired concentration. The resulting mixtures are solutions, suspensions, emulsions and other such mixtures, and can be formulated as a non-aqueous or aqueous mixture, including but not limited to, a solution, suspension, paste, gel, aerosol, spray, or any other formulation suitable for systemic administration.

Generally, the ammonia lowering agent is prepared in view of approval from a regulatory agency or otherwise prepared in accordance with generally recognized pharmacopeia for use in animals and in humans. The composition can include carriers such as a diluent, excipient, or vehicle. Such pharmaceutical carriers can be sterile liquids, such as water and oils. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A phenylacetic acid, or a pharmaceutically acceptable salt thereof composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents. Other examples of suitable pharmaceutical carriers will be known to those skilled in the art.

The ammonia lowering agent can be administered by any method and route that delivers the compound to the body. In certain embodiments, the ammonia lowering agent can be administered parenterally. A skilled artisan would readily understand and be able to select appropriate modes of administration or delivery, including, but not limited to, oral, intravenous, intramuscular, intradermal, transdermal, subcutaneous, or intraperitoneal administration, as well as by any combination of any two or more thereof, formulated in a manner suitable for each route of administration.

As well as in pharmaceutical compositions, the ammonia lowering agent may also be formulated or administered in other ways, for example in a nutritional composition such as a dietary supplement, for example a parenteral nutrition composition (e.g. alone or alongside other supplement ingredients). Suitably, such a composition may be for oral or non-oral administration.

As mentioned, the ammonia lowering agent is for administration in combination with GS protein. It will be appreciated that the ammonia lowering agent may be administered separately, sequentially or simultaneously with the GS protein, including in the same formulation or composition, or in a separate composition or formulation. Thus, in one exemplary embodiment the ammonia lowering agent may be administered orally, or by other systemic means and the GS may be administered by non-oral systemic means.

Exemplary therapeutically effective doses of the ammonia lowering agent, include but are not limited to, from about 1 mg/kg body weight per day to or to about 2000 mg/kg body weight per day, including from or from about 10 mg/kg to or to about 1000 mg/kg body weight per day, or from or from about 100 mg/kg to or to about 500 mg/kg body weight per day. Thus, for example, a subject can be administered 1, 2, 3, 4, 5, 10, 20, 30, 40, 50, 60, 70, 80, 90, 100, 150, 200, 250, 300, 350, 400, 450, 500, 550, 600, 650, 700, 750, 800, 850, 900, 950, 1000, or 2000 mg or more of the ammonia lowering agent per kg body weight per day. Other exemplary therapeutically effective doses of the ammonia lowering agent, include but are not limited to, from about 1 g/day to about 50 g/day. Thus, for example, a subject can be administered 1, 2, 3, 4, 5, 10, 20, 30, 40, or 50 grams, or more of the ammonia lowering agent per day. It will be appreciated that the effective dose may vary depending on the ammonia lowering agent. The GS composition, and/or the composition comprising the ammonia lowering agent or composition comprising a further agent which is not an ammonia lowering agent, if desired, can be presented in a package, in a kit or dispenser device, such as a syringe with a needle, or a vial and a syringe with a needle, which can contain one or more unit dosage forms. The kit or dispenser device can be accompanied by instructions for administration. In an embodiment where the GS composition and the composition comprising the ammonia lowering agent are separate, the kit may comprise the GS composition and the composition comprising the ammonia lowering agent. Suitably, in such an embodiment, the kit may comprise a GS composition, and a nitrogen scavenger. Suitably, in such an embodiment, the kit may comprise a GS composition, and a composition comprising phenylacetate, for example sodium phenylacetate. The compositions can be packaged as articles of manufacture containing packaging material, the composition, and a label that indicates that the composition is for administration to subjects for the treatment of hyperammonemia or a disease or condition associated with hyperammonemia.

In a further aspect, the invention provides an expression vector encoding glutamine synthetase or a biologically active fragment or variant thereof, for use in the treatment or prevention of hyperammonemia, wherein the vector is for systemic administration.

In a suitable embodiment, the vector further encodes an ammonia lowering agent.

In another aspect, the invention provides an expression vector encoding glutamine synthetase or a biologically active fragment or variant thereof, for use in combination with an ammonia lowering agent, for use in the treatment or prevention of hyperammonemia.

In another aspect, the invention provides an ammonia lowering agent for use in combination with an expression vector encoding glutamine synthetase or a biologically active fragment or variant thereof, for use in the treatment or prevention of hyperammonemia.

In another aspect, the invention provides a cell comprising an expression vector selected from the group consisting of: an expression vector encoding glutamine synthetase or a biologically active fragment or variant thereof, for use in the treatment of hyperammonemia, and an expression vector encoding glutamine synthetase or a biologically active fragment or variant thereof, for use in combination with an ammonia lowering agent, for use in the treatment or prevention of hyperammonemia.

In another aspect, the invention provides use of an expression vector encoding glutamine synthetase or a biologically active fragment or variant thereof, for the manufacture of a composition for the treatment or prevention of hyperammonemia, wherein the composition is for systemic administration.

In another aspect, the invention provides use of an expression vector encoding glutamine synthetase or a biologically active fragment or variant thereof, for the manufacture of a composition, for use in combination with an ammonia lowering agent, for the treatment or prevention of hyperammonemia.

In another aspect, the invention provides use of an ammonia lowering agent for the manufacture of a composition, for use in combination with an expression vector encoding glutamine synthetase or a biologically active fragment or variant thereof, for use in the treatment or prevention of hyperammonemia.

In another aspect, the invention provides a method of treating or preventing hyperammonemia in a subject, said method comprising systemic administration of an expression vector encoding glutamine synthetase or a biologically active fragment or variant thereof.

In another aspect, the invention provides a method of treating or preventing hyperammonemia in a subject, said method comprising administration of an expression vector encoding glutamine synthetase or a biologically active fragment or variant thereof, and an ammonia lowering agent.

In another aspect, the invention provides a composition comprising an expression vector encoding glutamine synthetase or a biologically active fragment or variant thereof, for use in the treatment or prevention of hyperammonemia, wherein the composition is for systemic administration.

In a suitable embodiment, the composition may further comprise an ammonia lowering agent.

In another aspect, the invention provides a composition comprising an expression vector encoding glutamine synthetase or a biologically active fragment or variant thereof, for use in combination with an ammonia lowering agent, for use in the treatment or prevention of hyperammonemia.

In another aspect, the invention provides a composition comprising an ammonia lowering agent, for use in combination with an expression vector encoding glutamine synthetase or a biologically active fragment or variant thereof, for use in the treatment or prevention of hyperammonemia.

In another aspect, the invention provides a kit comprising a with an expression vector encoding glutamine synthetase or a biologically active fragment or variant thereof, and a further therapeutic agent. Suitably, the further therapeutic agent may be an agent that is effective against hyperammonemia. Suitably the agent that is effective against hyperammonemia is an ammonia lowering agent or an amino acid or urea cycle intermediate thereof.

In another aspect, the invention provides a product comprising an expression vector encoding glutamine synthetase or a biologically active fragment or variant thereof and a further therapeutic agent, as a combined preparation for separate, simultaneous or sequential use in treating or preventing hyperammonemia. Suitably, the further therapeutic agent may be an agent that is effective against hyperammonemia. Suitably the agent that is effective against hyperammonemia is an ammonia lowering agent or an amino acid or urea cycle intermediate thereof. More suitably, the further therapeutic agent is a nitrogen scavenger.

In a suitable embodiment, the expression vector may be viral or non-viral. By way of example, a suitable viral expression vector may be derived from a virus selected from the group consisting of paramyxovirus, retrovirus, adenovirus, lentivirus, pox virus, alphavirus, and herpes virus. Other suitable viral vectors will be known to those skilled in the art.

Suitable non-viral expression vectors may be selected from the group consisting of inorganic particle expression vectors (such as calcium phosphate, silica, and gold), lipid based particle expression vectors (for example cationic lipids, lipid nano emulsions, and solid lipid nanoparticles) and polymer based particle expression vectors (for example peptides, polyethylenimine, chitosan, and dendimers). Other suitable non-viral expression vectors will be known to those skilled in the art.

Suitable systemic administration methods will be known to those skilled in the art. By way of example, systemic administration may be achieved by parenteral route of administration, such as intravenous or subcutaneous route. It will be appreciated that "systemic administration" allowed the product (such as glutamine synthetase or a biologically fragment thereof) of an expression vector to be expressed within multiple sites in the patient. In the context of the present invention, systemic administration does not include intramuscular administration.

The term "biologically active" refers to a fragment or variant of the nucleic acid encoding glutamine synthetase (SEQ ID NO: 1) exhibiting the ability to convert glutamate to glutamine. The protein according to SEQ ID NO: 1 is encoded by the nucleic acid sequence according to SEQ ID NO: 2. Thus, it will be appreciated that the vector, may comprise a fragment or variant of SEQ ID NO: 2 which encodes a biologically active fragment or variant of glutamine synthetase.

The term "variant" as used herein refers to a polypeptide comprising an alteration of the primary structure of the polypeptide of SEQ ID NO: 1. Suitably, a variant may share 70% or more identity with the polypeptide of SEQ ID NO: 1; 80% or more identity with the polypeptide of SEQ ID NO: 1; 90% or more identity with the polypeptide of SEQ ID NO: 1; 95% or more identity with the polypeptide of SEQ ID NO: 1; 96% or more identity with the polypeptide of SEQ ID NO: 1; 97% or more identity with the polypeptide of SEQ ID NO: 1; 98% or more identity with the polypeptide of SEQ ID NO: 1; or even 99% or more identity with polypeptide of SEQ ID NO: 1. A variant may differ from the polypeptide of SEQ ID NO: 1 by 1% or more, 2% or more, 3% or more, 4% or more, 5% or more, 10% or more, 20% or more, or even 30% or more with reference to sequence according to SEQ ID NO: 1.

The term "fragment" as used herein refers to a polypeptide comprising an alteration to the length of the primary structure of the polypeptide of SEQ ID NO: 1. A suitable fragment may comprise at least 60%, at least 65%, at least 70%, at least 75%, at least 80%, at least 85%, at least 90%, or at least 95% of the full length of SEQ ID NO: 1. Indeed, a suitable variant may comprise at least 96%, at least 97%, at least 98%, or at least 99% of SEQ ID NO: 1.

It will be appreciated that (except where the context requires otherwise), embodiments described with reference to the GS protein for use in preventing hyperammonemia, the GS protein for use in combination with an ammonia lowering agent, ammonia lowering agent for use in combination with a GS protein, their uses, methods of treatment, compositions, kit and product, will generally be applicable, to the remaining aspects of the invention.

BRIEF DESCRIPTION OF THE DRAWINGS

The present invention will now be further described with reference to the following non-limiting Examples and Figures in which.

EXAMPLES

Example 1

Production and Purification of GS Protein and GS Protein-PEG Conjugates

Production of human glutamine synthetase (GS): pET30a+ vector, containing the gene for human GS (SEQ ID NO: 5 comprising a 5' sequence encoding a His-tag and the linker GGGGS at the N-terminal end of the GS and codon optimised for expression in bacteria) was used in an *E. coli* expression system. After plasmid construction, evaluation for the expression of GS was performed with a wide range of induction (IPTG) and expression temperatures. Human GS was solubly expressed in the construct as detected by SDS-PAGE. Lysis buffer (50 mM Tris pH 8.0, 10% glycerol, 0.1% Triton X-100, 100 µg/ml lysozyme, 1 mM PMSF, 3

Units DNAse, 2 mM MgCl) was used to extract soluble protein from cells. Soluble protein was extracted following centrifugation. After expression studies, the best condition found with BL21 (DE3) cells, cultured and induced with 0.1 mM IPTG at 25° C. for 16 hours. Other conditions tried, included using varied IPTG induction (from 0.01M-0.1M IPTG), various incubation temperatures (ranging from 16° C.-37°), and induction incubation times from 4-16 hours.

Purification of the expressed GS: the first step purification of the expressed protein comprised His tag purification with Ni-NTA beads, washing with 20 mM Imidazole, and elution with 300 mM Imidazole.

Protein PEG conjugation: the GS protein was conjugated under reducing conditions (with the use of 20 mM Sodium Cyano borohydride) to N-terminal aldehyde 20 kDa peg for 16 hours (Dr Reddy's 20 kDa N-terminal Aldehyde PEG).

Figure 1:
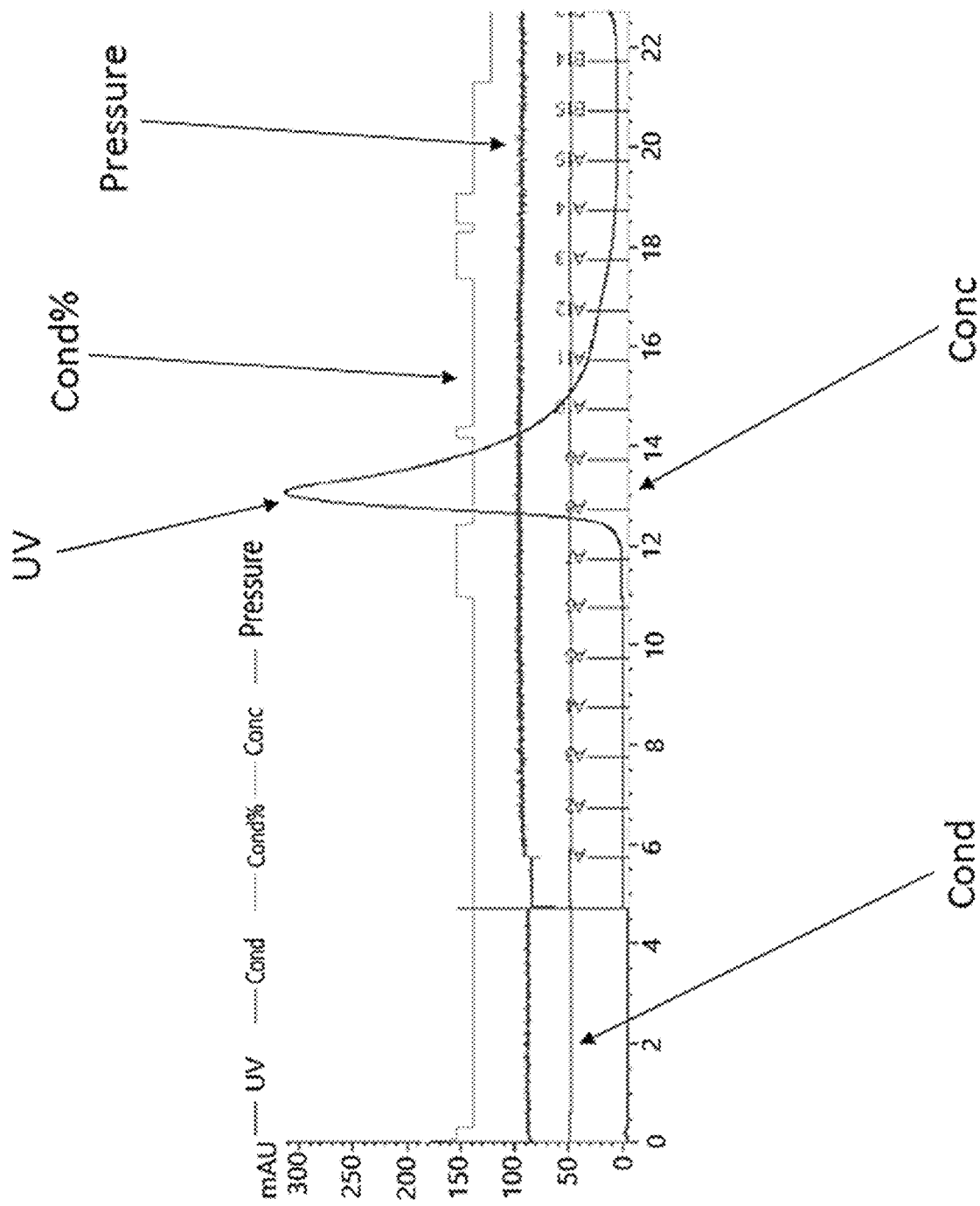
FIG. 1 shows the results of size exclusion chromatography (SEC) on a Superose 12 column of 20 kDa N-terminal aldehyde PEG conjugates of human GS protein as prepared in Example 1. The graph shows that multimers were eluted in fractions 8 and 9, and monomer in fraction 10.

Final purification: Conjugated protein was further purified using SEC chromatography. A Superose 6 or Superose 12 column (see FIG. 1) was used. Multimers were found in fractions 8+9. Fraction 10 in Superose 12 comprised (dilute) multimer. In Superose 6, multimers were found in fractions 8+9 and monomer in fractions 12/13.

A final formulation of the GS in PBS, pH 7.4 containing trehalose and sucrose was prepared.

Example 2

Activity of GS Preparations

Various GS preparations and PEG conjugates prepared according to Example 1 were tested for GS activity using the assay of Acosta et al., 2009 (supra), modified from the original assay described in Ehrenfeld et al., 1963, J. Biol. Chem. 238 (11), 3711-3716.

Figure 2:
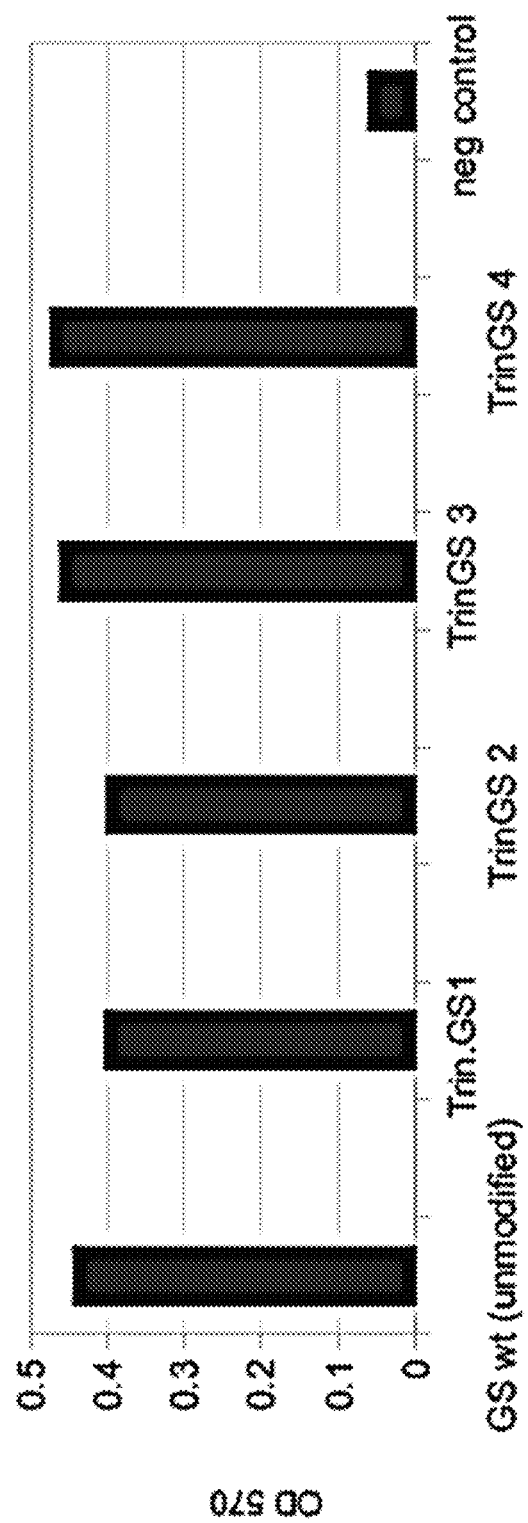
FIG. 2 shows a comparison of the in-vitro GS activity of various GS candidates: PEG-conjugated variants (Trin GS1, Trin GS2, Trin GS3, Trin GS 4) versus non-conjugated GS (wt GS) and negative control. Glutamine Synthetase activity is shown as OD 570 nm according to the assay of Acosta et al., 2009, World J. Gastroenterol., 15 (23), 2893-2899. Trin GS1-(N-term Ald monomer); Trin GS2-Nof-20; Trin GS3-Nof-30, Trin GS4-N-term Ald multimer.

100 ug of purified protein sample was added to the following reaction buffer: 150 µL stock solution (100 mmol/L imidazole-HCl buffer [pH7.1], 40 mmol/L MgCl2, 50 mmol/L, β-mercaptoethanol, 20 mmol/L ATP, 100 mmol/L, glutamate and 200 mmol/L hydroxylamine, adjusted to pH 7.2) Tubes were incubated at 37° C. for 15 min. The reaction was stopped by adding 0.6 mL [2× concentration] ferric chloride reagent (0.37 mol/L FeCl3, 0.67 mol/L HCl and 0.20 mol/L trichloroacetic acid). Samples were placed for 5 minutes on ice. Precipitated proteins were removed by centrifugation at 10,000 g, and the absorbance of the supernatants was read at 535-570 nm against a reagent blank. The results are shown in FIG. 2. Trin1—(N-term Aldehyde monomer PEG of 20 kD size, obtained from Dr Reddy's); Trin2—Nof-20 conjugated GS, which was conjugated to the GS protein with a monofunctional linear 20 kD PEG, NHS active ester, obtained from NOF corporation); Trin 3—Nof-30, conjugated to the GS protein with a monofunctional linear 30 kD PEG, NHS active ester, obtained from NOF corporation) Trin4—N-term Ald, GS multimers). Trin 4 (N-term Ald multimer) showed the best activity, with a very similar activity profile compared to the wt GS (non-conjugated), though activity of other conjugates was similar.

Example 3

Figure 3:
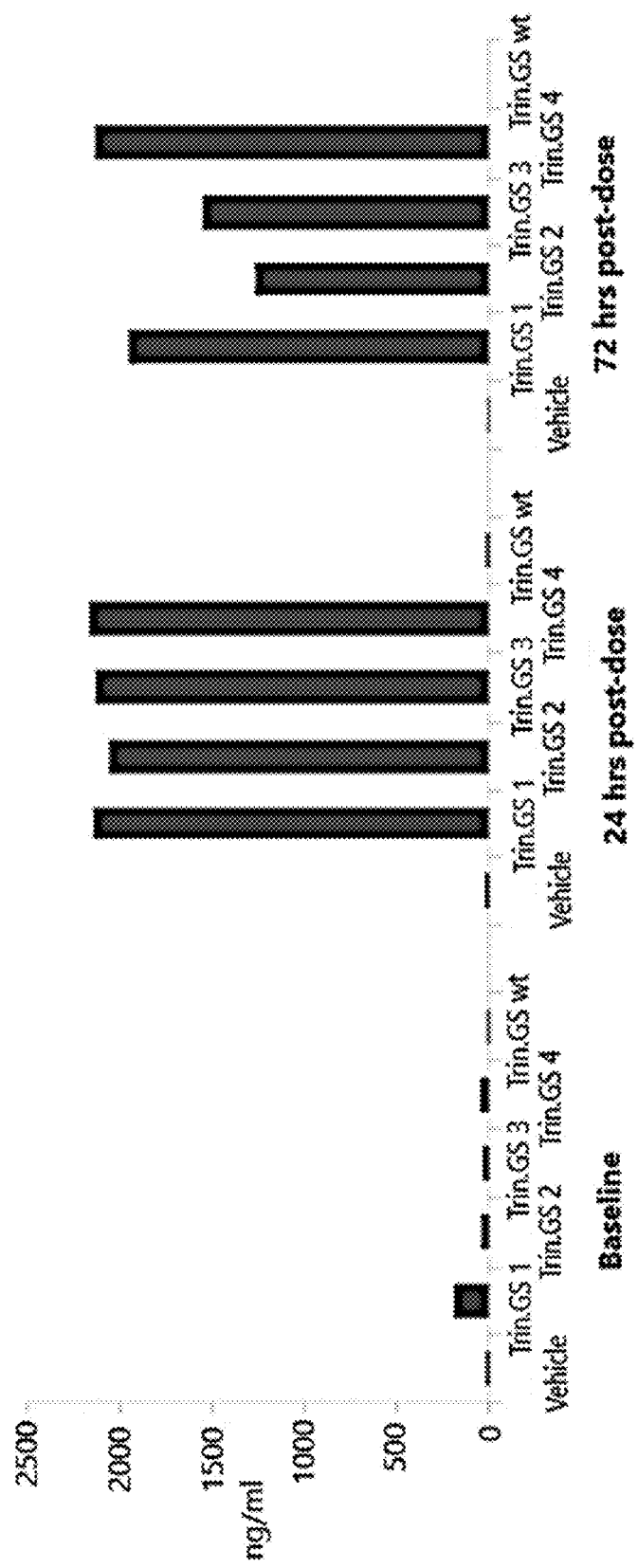
FIG. 3 shows PEG ELISA results on plasma pre- and post-dosing of male, wild-type (wt) CD1 mice of various conjugates at (A) baseline, (B) 24 hours post-dose and (C) 72 hours post-dose. (Trin1—N-terminal Aldehyde conjugated GS monomer; Trin2—Nof-20 GS conjugated multimer; Trin 3—Nof-30 conjugated GS multimer; Trin4—N-terminal Aldehyde conjugated PEG multimer)

Dosing of GS Protein to Mice-Effects on Plasma Levels of GS Protein-PEG Conjugates Male, wild-type (wt) CD1 mice were dosed at 2.5 mg/kg with subcutaneous (s.c) dosing of various GS protein and PEG conjugates prepared as described in Example 1 (Trin1—N-terminal Aldehyde conjugated GS monomer; Trin2—Nof-20 GS conjugated multimer; Trin 3—Nof-30 conjugated GS multimer; Trin4—N-terminal Aldehyde conjugated PEG multimer). The ELISA was conducted according to the protocol outlined by the manufacturer (Abcam PEG ELISA kit, ab 133065). Results of the plasma ELISA, as shown in FIG. 3, show either very low or undetectable levels for unconjugated wt GS, as expected at all timepoints. After 24 hours, several candidates were found to be at a high level in plasma; however, after 72 hours post-dosing, Trin-GS 4 (N-terminal Aldehyde conjugated PEG GS multimer) showed the highest presence. N=2 animals in each group. Thus, this experiment shows that systemic administration of GS protein may be used successfully to obtain high circulating levels of the GS PEG conjugates, and in particular at levels which may be therapeutically effective or active.

Example 4

Dosing of GS Protein to Mice-GS Activity Levels of Liver Lysates

Figure 4:
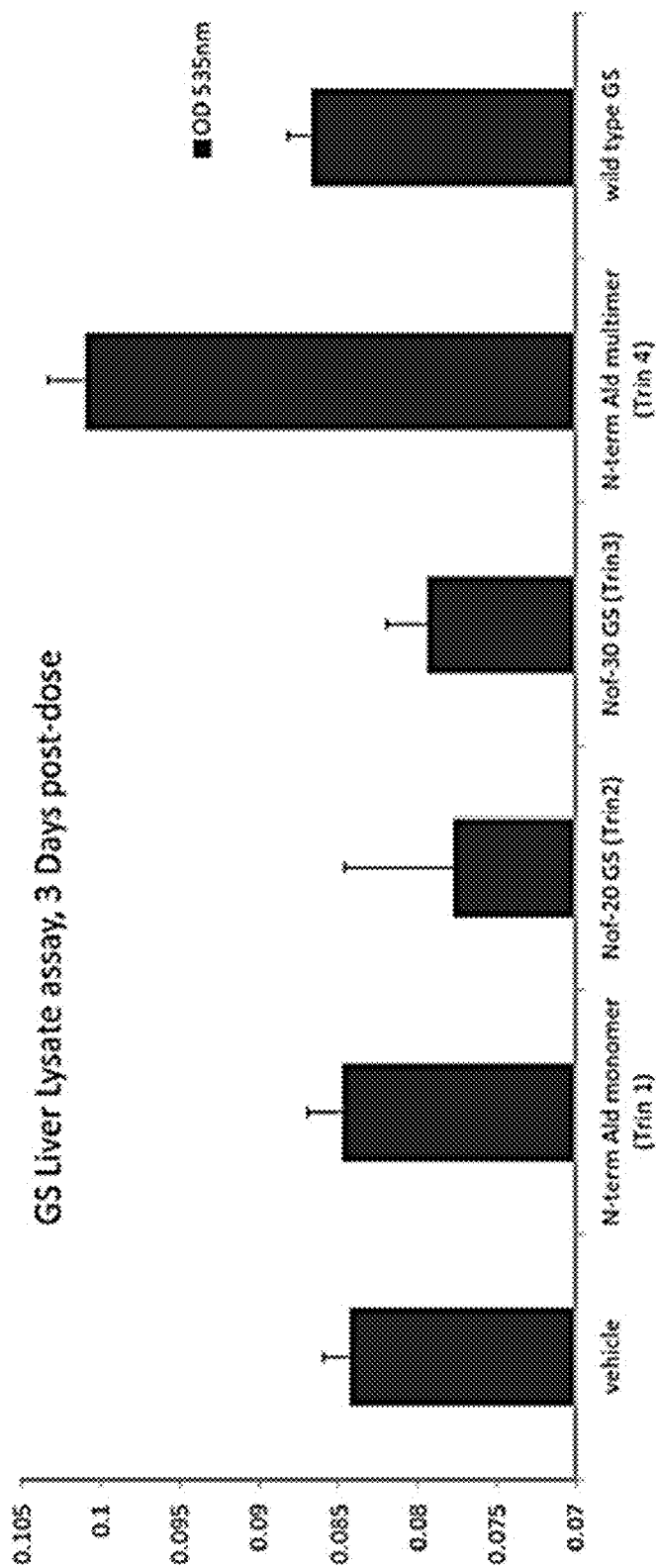
FIG. 4 shows GS activity (OD 535 nm) results in liver lysates in dosed wtCD1 mice at 2.5 mg/kg, 3 days post-dosing, as described in Example 3.

The activity assay was performed as described in Example 2, with the exception that 500 µg of liver lysate (from culled mice from the experiment of Example 3) was added to each reaction where appropriate. The results are shown in FIG. 4. The GS activity results in liver lysates 3 days post-dosing demonstrate that the superior candidate was the N-terminal aldehyde conjugated PEG GS multimer, which was the only candidate to show significant activity above baseline compared to the vehicle (saline-dosed) control. N=2 animals in each group.

Example 5

The Otc$^{spf-ash}$ Mouse model of urea cycle disorder (OTC deficiency) was used to show the effects of GS and GS+SP. The details of the mice used can be found at https://www.jax.org/strain/001811 (B6EiC3Sn a/A-Otc$^{spf-ash}$/J). They are fed normal chow. The ages were variable from about 10 weeks to 23 weeks, with groups well-matched. All animals are male hemizygous (as OTC is X-linked, it is present only on the X chromosome of the males, therefore the mice are knockout).

All groups (vehicle, GS and GS+SP; where GS=Glutamine synthetase, GS+SP=Glutamine Synthetase+Sodium Phenlyacetate) were treated as follows:

The experiment ran from a Tuesday until the following Wednesday (8 days).

SP was dosed i.p. 350 mg/kg twice daily; GS was dosed in all treated groups for the first 4 days (i.p. @ 40 mg/kg once daily), then a break of 2 days [a weekend], and 3 more days of dosing with GS @ 40 mg/kg i.p.

Mice were culled on day 8, and blood extracted, spun down for plasma, and this plasma was used for ammonia quantitation (see method below).

Genotyping is performed using standard methods described in the literature.

Materials and Methods

All experiments were performed in accordance with the Animals (Scientific Procedures) Act of 1986, which was revised according to the European Directive2010/63/EU. All animals received humane care according to the criteria outlined in the Guide for the Care and Use of Laboratory Animals (National Institutes of Health publication 86-23; revised 1985). All the animals used in these experiments were Male Sprague-Dawley rats (body weight, 250 g at the beginning of the experiments) were obtained from Charles River Laboratories (Kent, UK) and divided into 5 groups:

bile duct ligated animals+ammonia+saline serum (BDL+ HA+SS, n=6), bile duct ligated animals+ammonia+sodium phenylacetate (BDL+HA+SP, n=6), bile duct ligated animals+ammonia+sodium phenylacetate+glutamine synthetase (BDL+HA+SP+GS, n=5), bile duct ligated animals+ammonia+glutamine synthetase (BDL+HA+GS, n=6), sham-operated animals+glutamine synthetase (SHAM+GS, n=5). Treatment comprising SP and GS may be referred to as "COMBO".

Bile Duct Ligation Surgery

Under general anesthesia (5% isoflurane in 100% oxygen for induction, 2% isofluorane in air for maintenance) rats underwent triple ligation of the bile duct (way of a small laparotomy) to induce chronic liver injury and were studied 28 days after surgery. A midline abdominal incision was made under anesthesia. In the BDL group, the common bile duct was isolated, triply ligated with 3-0 silk, and sectioned between the ligatures. The sham-operated group performed the same procedure without the sectioning between the ligatures. After BDL all animals continued to gain weight and were comparable with sham controls. The overall mortality in both groups was less than 10% and occurred within 36 hours of the operation.

Noncirrhotic Hyperammonemia Condition

Twenty-three rats were administered a hyperammonemia (HA) diet. The amino acid recipe used for a stock of approximately 100 g was: 15 g leucine, 7.7 g phenylalanine, 7 g glutamate, 10 g alanine, 4.4 g proline, 5.8 g threonine, 11 g aspartate, 5 g serine, 4.8 g glycine, 3.3 g arginine, 9.6 g lysine, 8.4 g histidine, 3 g tyrosine, 1.5 g tryptophan, and 10.6 g valine. 25 g of this mix (mixed 1:5 with standard rodent chow powder) was freshly prepared daily and rats were given free access to it for 5 days. The recipe approximates the amino acid composition of a rodent haemoglobin, [1] mimicking the effect of gastrointestinal bleeding, which is known to result in systemic hyperammonemia [2].

Sodium Phenylacetate Condition

Eleven rats were administered a sodium phenylacetate (SP) diet. 0.3 g/kg a day for 5 days was mixed with the chow powder and freshly prepared daily.

Glutamine Synthetase Condition

Sixteen rats were injected with GS intraperitoneally every two days (day 1 and day 3). The total volume injected was 3 mls i.p., which allows for 18-22 mg/kg of GS.

Blood Sampling and Biochemistry

Plasma samples were collected from the leg vein at different timepoints in all groups. The timepoints were counted after the treatment with glutamine synthetase as follows: 6 hours, 24 hours, 48 hours and 5 days. Analyses were conducted for plasma ammonia levels in every timepoint using 200 µl of respective plasma using a Cobas Integra 400 multi-analyser with the appropriate kits (Roche-diagnostics, Burgess Hill, West Sussex, UK).

Brain Edema

This was measured using the dry weight technique as described previously [3, 4]. Briefly, oven dried Eppendorf's were weighed with a sensitive electronic scale, then prefrontal cortex, striatum, hippocampus, cerebellum and cortices of each animal were placed into each respectively labelled Eppendorf and reweighed; all samples where within 0.1 mg difference. The dry weight was determined after Eppendorf's loaded with individual brain samples were dried in an oven at 60° C. for 7 days. Tissue water content was then calculated as % H2O=(1-dry wt/wet wt)×100%.

Test for Assessment Locomotor Activity: RotaRod-Accelerod Test

This test of motor performance consists of a motor-driven rotating rod that enables us to assess motor coordination and resistance to fatigue (Jones and Roberts 1968). The accelerating rotarod 7750 of Ugo Basile (Ugo Basile Biological Research Apparatus, Italy) was used for the rats. The procedure followed has two parts. In the first one, the animals were placed in the apparatus and the speed was maintained constant at 2 rpm for 60 s. In the second part, the rats were evaluated for 5 min in the accelerod test session, in which the rotation rate constantly increased until it reached 20 rpm. Latency to fall off the rod and the actual rotation speed were recorded in the pre- and post-treatment conditions for all groups after 1 hour treatment.

Ammonia Determination in Blood Using the TCA Direct Method

The method described in the paper (Clin Chim Acta. 1968 October; 22 (2) 183-86) was used to measure plasma ammonia concentration, as follows.

Principle

In an alkaline solution ammonium ions react with hypochlorite to form monochloramine. In the presence of phenol and an excess of hypochlorite, the monochloramine will form a blue coloured compound, indophenol, when nitroprusside is used as a catalyst. The concentration of ammonium is determined spectrophotometrically at 630 nm.

Method

Dissolve 3.5 g of phenol and 0.04 g sodium nitroprusside in 100 ml distilled water to prepare reagent A.

Dissolve 1.8 g sodium hydroxide in 48 mls in distilled water and add 4 mls of 1M sodium hypochlorite solution to prepare reagent B.

Add 150 µl of 5% TCA to 50 µl to each plasma sample and centrifuge at 10,000 RPM at 4° C. for 10 minutes. Take 50 µl of the supernatant and put in 96 well plate to which is added 50 µl of both reagents A and B.

Standard ammonium chloride concentrations for the calibration curve are made by dissolving ammonium chloride in distilled water and serially diluting to make concentrations ranging from 400 µmol to 3 µmol. Distilled water is used as the blank The well plate is covered from light and incubated at 50° C. for 60 minutes. Absorbance is measured at 630 nm using a spectrophotometer to determine the ammonia concentration.

Results

Dosing of GS Protein to Mice—GS Activity Levels in Liver and Blood

Figure 5A:
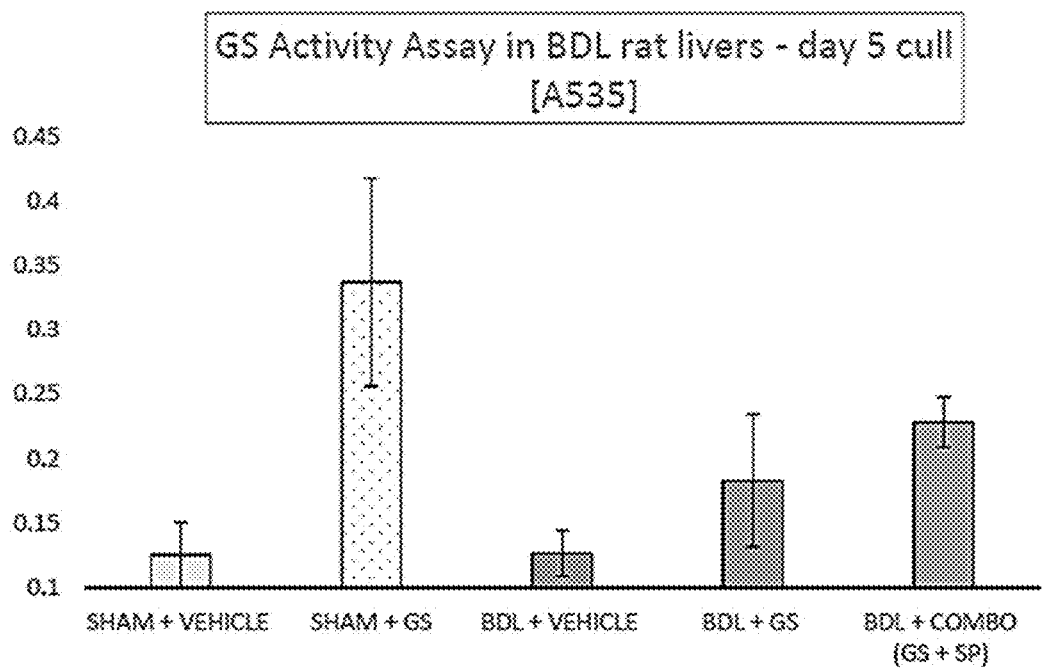
FIG. 5A shows liver GS activity assay results.
Figure 5B:
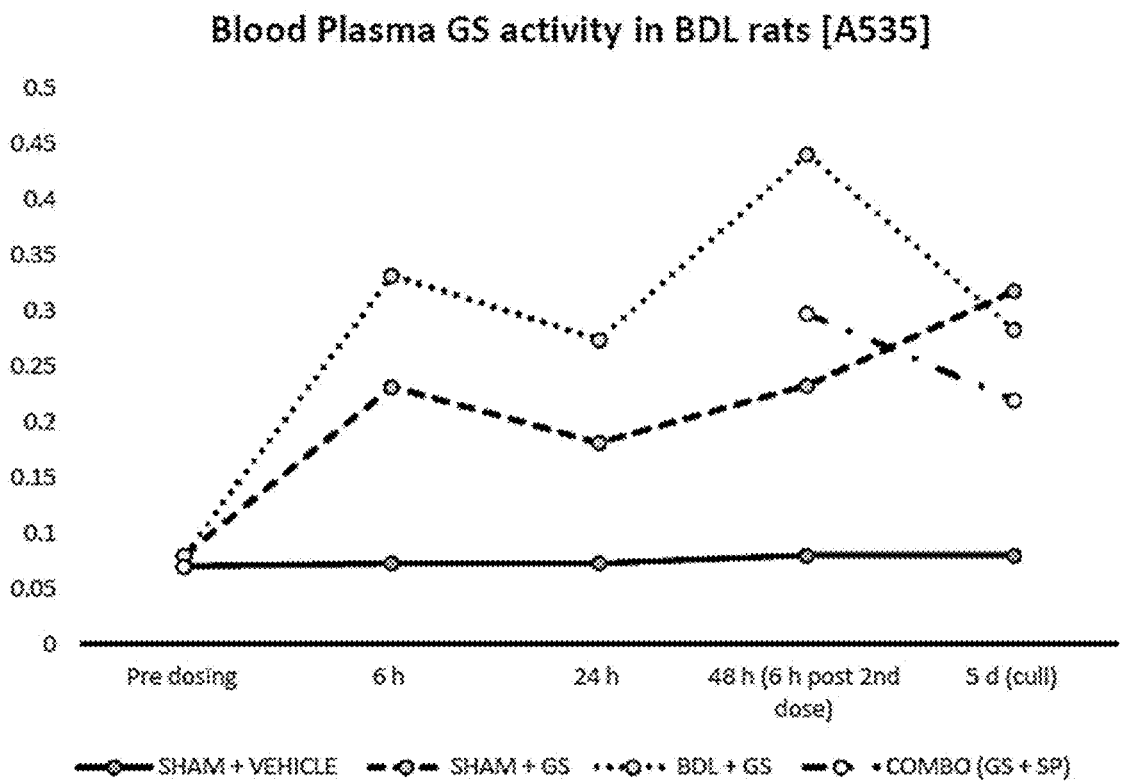
FIG. 5 B shows blood plasma GS activity assay results. Both, liver and blood plasma GS activity was assayed in BDL rats treated with GS protein, and GS protein with nitrogen scavenger.

The activity assay was performed as described in the materials and methods section above. The results are shown in FIGS. 5A and B. The results in rat liver measured at day 5, show that GS activity is best in the SHAM+GS group. Additionally, it can been seen from FIG. 5A that GS and GS+SP treatment increase GS activity in the livers of mice which have undergone BDL. When measured in blood, the results show that GS activity is best in the BDL+GS group. Additionally, from FIG. 5B, it can be seen that GS activity in blood is consistant over time, even 24 hrs and 48 hrs post dosing.

Dosing of GS Protein to Mice-Ammonia Concentrations in the BDL Rat

Figure 6:
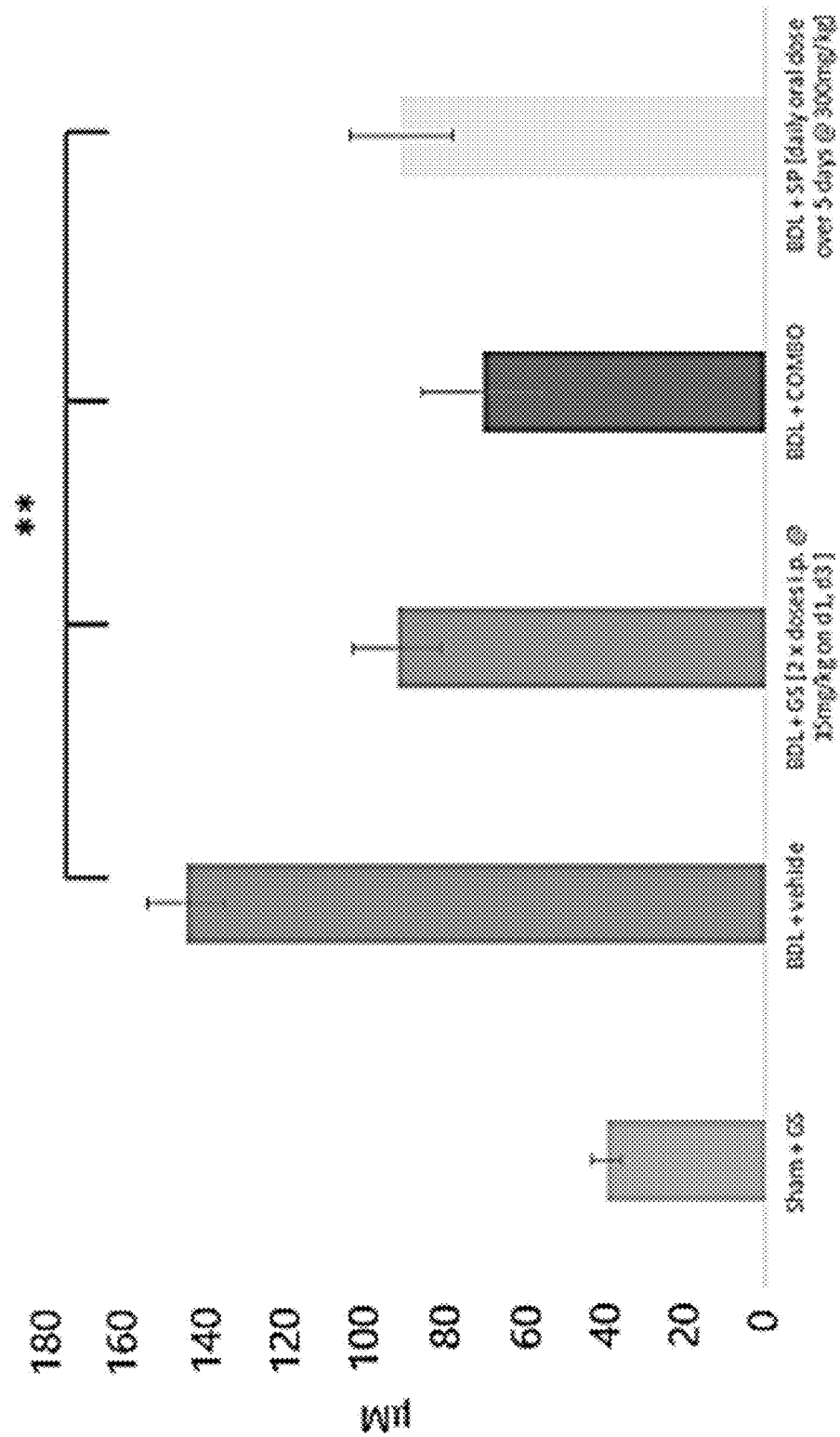
FIG. 6 illustrates ammonia blood levels measured in BDL rats treated with GS protein, and GS protein with nitrogen scavenger.

As seen in FIG. 6, ammonia levels are highest in the BDL rat. Treatment with GS, GS+SP, and SP, each resulted in a significant reduction of ammonia levels in the blood. GS reduced ammonia levels following 2 doses. Treatment with GS+SP reduced the ammonia levels most significantly, suggesting a synergistic effect.

Dosing of GS Protein to Mice-Brain Swelling in the BDL Rat

Figure 7:
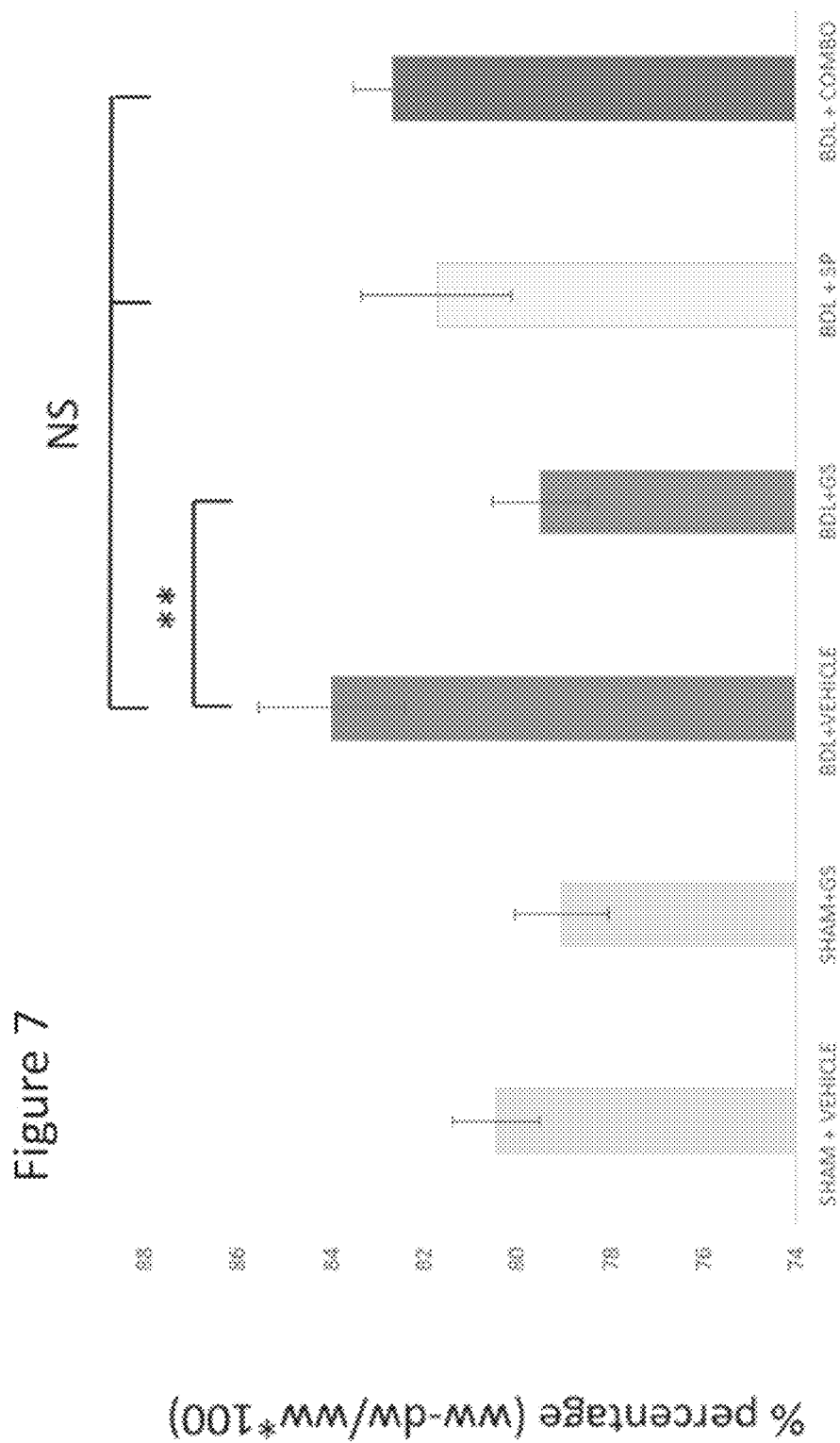
FIG. 7 illustrates a graph showing percentage of oedema in the prefrontal cortex in BDL rats treated with GS protein, or GS protein with nitrogen scavenger.

Brain oedema was measured in the prefrontal cortex. Treatment with GS was found to reduce brain oedema most significantly compared to treatment to with SP, and even treatment with SP+GC (FIG. 7). Treatment with SP did not statistically significantly reduce the swelling as compared to the control (i.e. BDL mice without treatment).

Dosing of GS Protein to Mice-Brain and Physical Function in the BDL Rat

Figure 8:
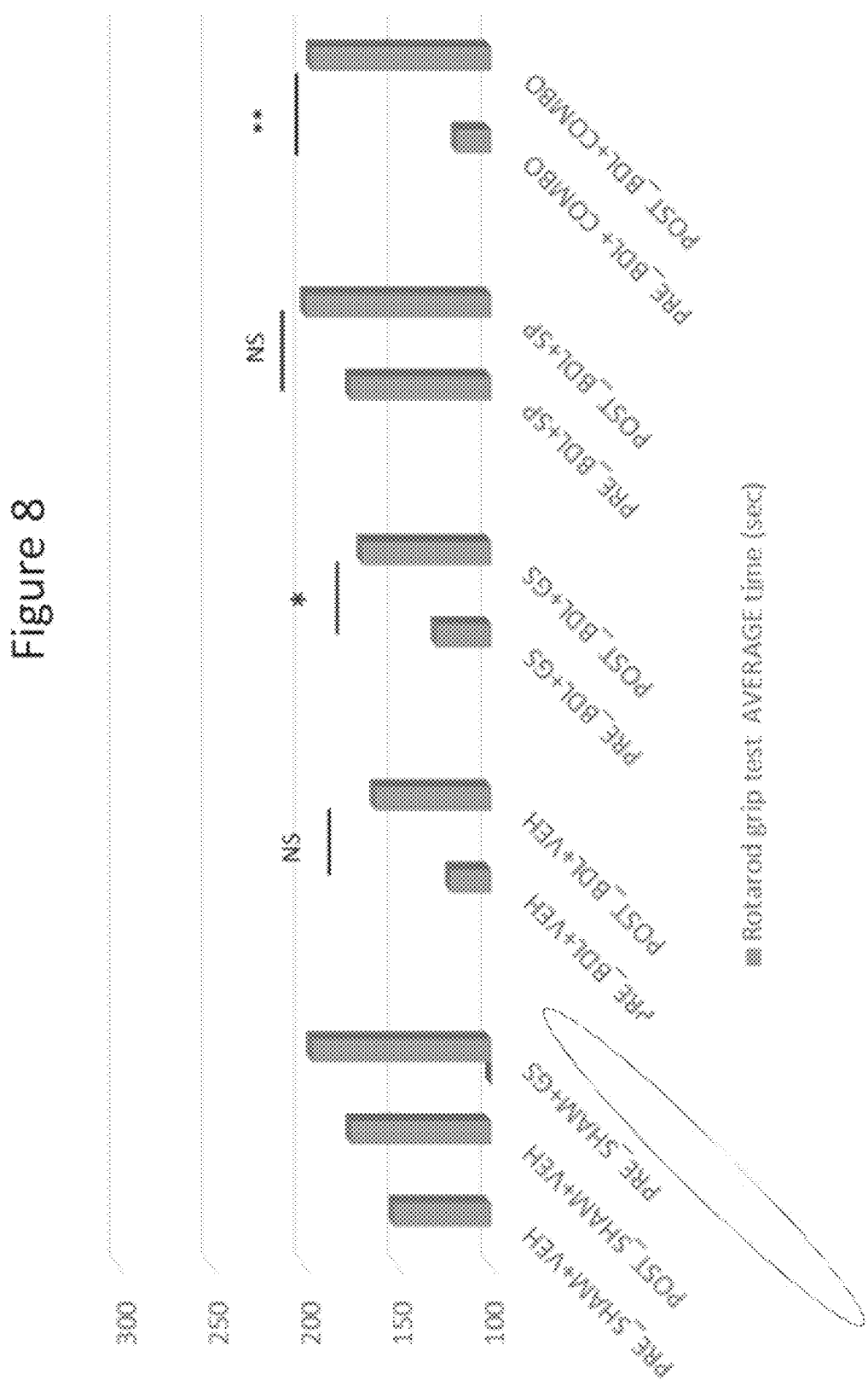
FIG. 8 shows the results of a rotarod grip test in BDL rats treated with GS protein, or GS protein with nitrogen scavenger.

FIG. 8 shows the results of a rotarod grip test. Surprisingly, GS dosing was found to improve performance in all tested mice groups. Treatment with SP alone did not lead to statistically significant effects, but treatment with GS+SP shows the best improvement, suggesting a synergistic effect.

Treatment of Mice with OTC Deficiency

Figure 9:
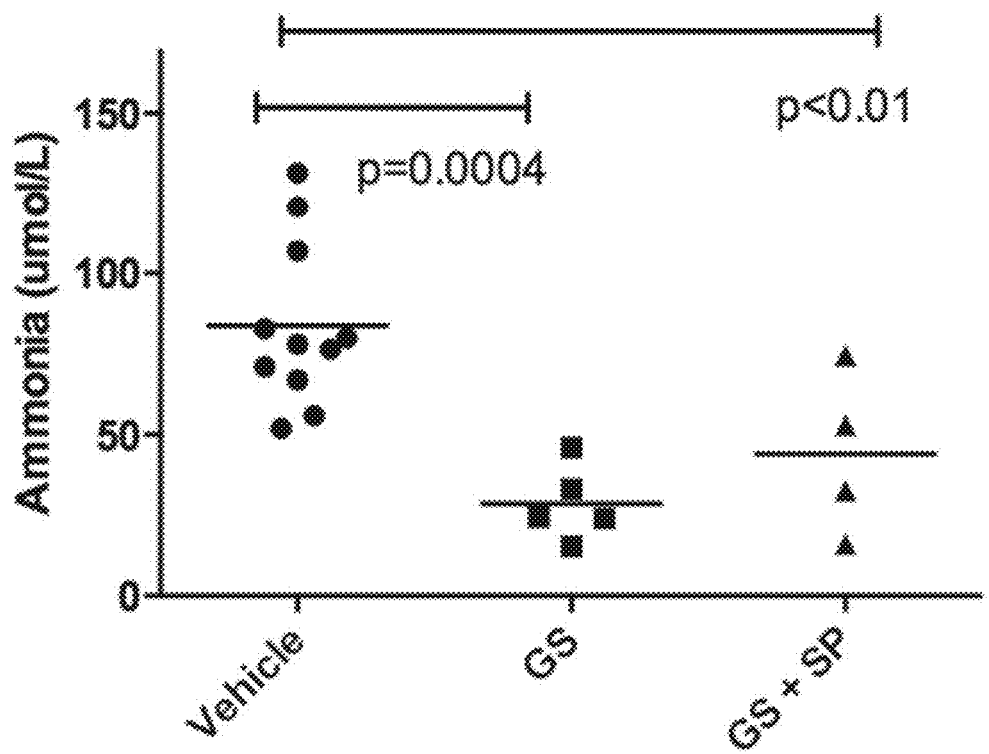
FIG. 9 a graph showing ammonia levels in OTC mice treated with GS protein, or GS protein with nitrogen scavenger (SP-sodium phenylacetate).

As shown in FIG. 9, ammonia is very significantly decreased in the treated groups.

Figure 10:
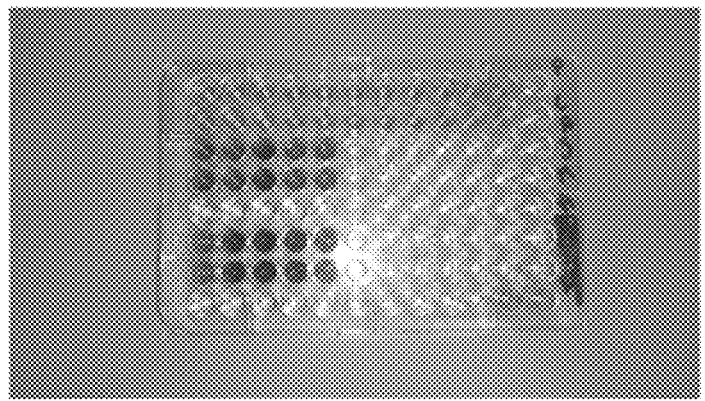
FIG. 10 shows the results of ammonia levels in plasma and liver GS activity in OTC mice treated with GS protein or DS protein with nitrogen scavenger (SP-sodium phenylacetate)
Figure 10:
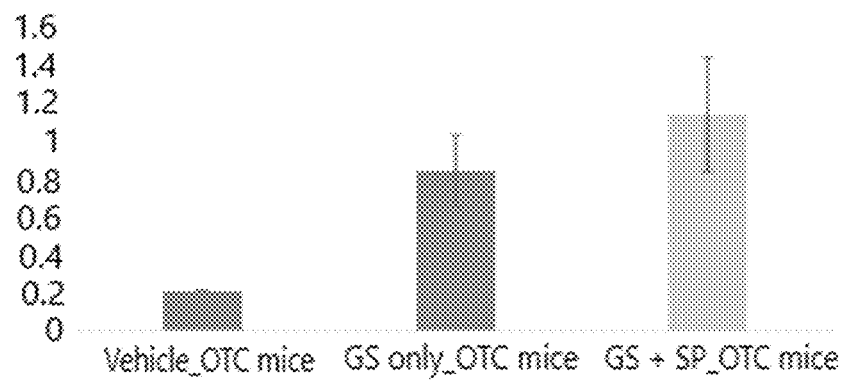
Figure 10:
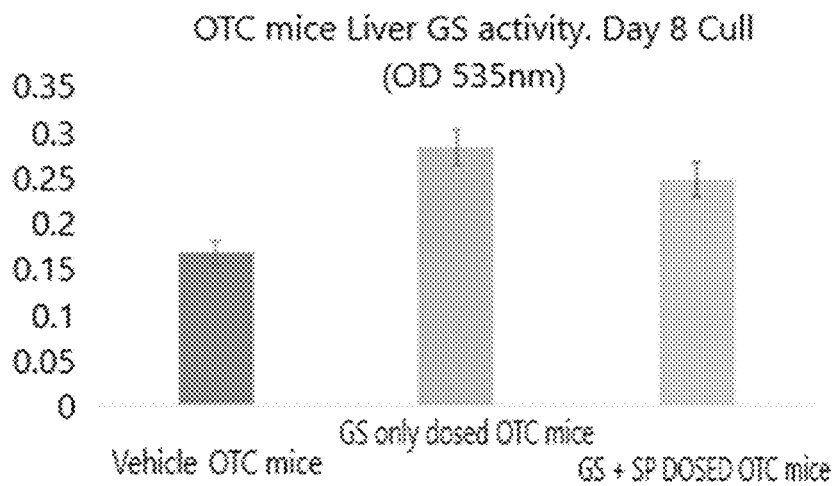

In FIG. 10, it is seen that in the OTC mice treated with GS or GS & SP, plasma GS activity increased from 0.2 in the vehicle group, to 0.8 in GS only group and ~1.1 in the GS & SP group. Liver GS activity increased from ~0.175 in the vehicle group, to ~2.8 in GS only group and ~2.5 in the GS & SP group Summary of Results In summary, the administered GS is biocompatible, safe and improves blood and liver GS activity. It also leads to a reduction in ammonia and brain oedema, as well as improves neurocognitive and/or physical function. Additionally, the data suggests that treatment with SP and GS may have a synergistic effect.

REFERENCES

[1] Riggs A. The amino acid composition of some mammalian hemoglobins: mouse, guinea pig, and elephant. J Biol Chem 1963; 238:2983-2987.
[2] Balata S, Olde Damink S W, Ferguson K, Marshall I, Hayes P C, Deutz N E, Williams R, Wardlaw J, Jalan R. Induced hyperammonemia alters neuropsychology, brain MR spectroscopy and magnetization transfer in cirrhosis. Hepatology 2003; 37:931-939.
[3] Stewart-Wallace A M. A biochemical study of cerebral tissue, and of changes in cerebral oedema. Brain 1939; 62:426-38.
[4] Traber P G, Ganger D R, Blei A T. Brain edema in rabbits with galactosamine-induced fulminant hepatitis. Regional differences and effects on intracranial pressure. Gastroenterology 1986; 91:1347-56.

BRIEF DESCRIPTION OF THE SEQUENCE LISTINGS

```
SEQ ID NO: 1 [Full human protein]
MTTSASSHLNKGIKQVYMSLPQGEKVQAMYIWIDGTGEGLRCKTRTLDSEPKCVEELPEW
NFDGSSTLQSEGSNSDMYLVPAAMFRDPFRKDPNKLVLCEVFKYNRRPAETNLRHTCKRI
MDMVSNQHPWFGMEQEYTLMGTDGHPFGWPSNGFPGPQGPYYCGVGADRAYGRDIVEA
HYRACLYAGVKIAGTNAEVMPAQWEFQIGPCEGISMGDHLWVARFILHRVCEDFGVIATF
DPKPIPGNWNGAGCHTNFSTKAMREENGLKYIEEAIEKLSKRHQYHIRAYDPKGGLDNAR
RLTGFHETSNINDFSAGVANRSASIRIPRTVGQEKKGYFEDRRPSANCDPFSVTEALIRTCLL
NETGDEPFQYKN SEQ ID. NO. 2 (ONLY Methionine is cleaved for the mature protein in vivo):
TTSASSHLNKGIKQVYMSLPQGEKVQAMYIWIDGTGEGLRCKTRTLDSEPKCVEELPEWNF
DGSSTLQSEGSNSDMYLVPAAMFRDPFRKDPNKLVLCEVFKYNRRPAETNLRHTCKRIMD
MVSNQHPWFGMEQEYTLMGTDGHPFGWPSNGFPGPQGPYYCGVGADRAYGRDIVEAHY
RACLYAGVKIAGTNAEVMPAQWEFQIGPCEGISMGDHLWVARFILHRVCEDFGVIATFDP
KPIPGNWNGAGCHTNFSTKAMREENGLKYIEEAIEKLSKRHQYHIRAYDPKGGLDNARRL
TGFHETSNINDFSAGVANRSASIRIPRTVGQEKKGYFEDRRPSANCDPFSVTEALIRTCLLNE
TGDEPFQYKN SEQ ID NO: 3 cDNA
CGAGAGTGGGAGAAGAGCGGAGCGTGTGAGCAGTACTGCGGCCTCCTCTCCTCTCCTAAC
CTGCTCTCGCGGCCTACCTTTACCCGCCCGCCTGCTCGGCGACCAGAACACCTTCCACCA
TGACCACCTCAGCAAGTTCCCACTTAAATAAAGGCATCAAGCAGGTGTACATGTCCCTGC
CTCAGGGTGAGAAAGTCCAGGCCATGTATATCTGGATCGATGGTACTGGAGAAGGACTGC
GCTGCAAGACCCGGACCCTGGACAGTGAGCCCAAGTGTGTGGAAGAGTTGCCTGAGTGGA
ATTTCGATGGCTCCAGTACTTTACAGTCTGAGGGTTCCAACAGTGACATGTATCTCGTGC
CTGCTGCCATGTTTCGGGACCCCTTCCGTAAGGACCCTAACAAGCTGGTGTTATGTGAAG
TTTTCAAGTACAATCGAAGGCCTGCAGAGACCAATTTGAGGCACACCTGTAAACGGATAA
TGGACATGGTGAGCAACCAGCACCCCTGGTTTGGCATGGAGCAGGAGTATACCCTCATGG
GGACAGATGGGCACCCCTTTGGTTGGCCTTCCAACGGCTTCCCAGGGCCCCAGGGTCCAT
ATTACTGTGGTGTGGGAGCAGACAGAGCCTATGGCAGGGACATCGTGGAGGCCCATTACC
GGGCCTGCTTGTATGCTGGAGTCAAGATTGCGGGACTAATGCCGAGGTCATGCCTGCCC
AGTGGGAATTTCAGATTGGACCTTGTGAAGGAATCAGCATGGGAGATCATCTCTGGGTGG
CCCGTTTCATCTTGCATCGTGTGTGTGAAGACTTTGGAGTGATAGCAACCTTTGATCCTA
AGCCCATTCCTGGGAACTGGAATGGTGCAGGCTGCCATACCAACTTCAGCACCAAGGCCA
TGCGGGAGGAGAATGGTCTGAAGTACATCGAGGAGGCCATTGAGAAACTAAGCAAGCGGC
ACCAGTACCACATCCGTGCCTATGATCCCAAGGGAGGCCTGGACAATGCCCGACGTCTAA
CTGGATTCCATGAAACCTCCAACATCAACGACTTTTCTGGTGGTGTAGCCAATCGTAGCG
CCAGCATACGCATTCCCCGGACTGTTGGCCAGGAGAAGAAGGGTTACTTTGAAGATCGTC
GCCCCTCTGCCAACTGCGACCCCTTTTCGGTGACAGAAGCCCTCATCCGCACGTGTCTTC
TCAATGAAACCGGCGATGAGCCCTTCCAGTACAAAAATTAAGTGGACTAGACCTCCAGCT
GTTGAGCCCCTCCTAGTTCTTCATCCCACTCCAACTCTTCCCCCTCTCCCAGTTGTCCCG
ATTGTAACTCAAAGGGTGGAATATCAAGGTCGTTTTTTTTCATTCC SEQ ID NO: 4: GS protein grown in bacteria, used in Example 1
MGSSHHHHHHGGGGSMTTSASSHLNKGIKQVYMSLPQGEKVQAMYIWIDGTGEGLRCKT
RTLDSEPKCVEELPEWNFDGSSTLQSEGSNSDMYLVPAAMFRDPFRKDPNKLVLCEVFKY
```

```
NRRPAETNLRHTCKRIMDMVSNQHPWFGMEQEYTLMGTDGHPFGWPSNGFPGPQGPYYC
GVGADRAYGRDIVEAHYRACLYAGVKIAGTNAEVMPAQWEFQIGPCEGISMGDHLWVAR
FILHRVCEDFGVIATFDPKPIPGNWNGAGCHTNFSTKAMREENGLKYIEEAIEKLSKRHQYH
IRAYDPKGGLDNARRLTGFHETSNINDFSAGVANRSASIRIPRTVGQEKKGYFEDRRPSANC
DPFSVTEALIRTCLLNETG DEPFQYKN

SEQ ID NO: 5 cDNA (bacterial optimised cDNA used in Example 1).
ATGGGCAGCAGCCACCACCATCACCACCACGGCGGCGGCGGTAGCATGACCACCTCGG
CAAGCAGCCACCTGAATAAAGGCATCAAACAGGTGTATATGTCTCTGCCGCAGGGTGA
AAAAGTTCAAGCCATGTACATTTGGATCGATGGCACCGGTGAAGGCCTGCGTTGCAAA
ACCCGCACGCTGGACTCAGAACCGAAATGTGTGGAAGAACTGCCGGAATGGAACTTTG
ATGGTAGCTCTACGCTGCAGTCGGAAGGCAGTAATTCCGACATGTATCTGGTTCCGGCG
GCCATGTTTCGTGATCCGTTCCGCAAAGACCCGAACAAACTGGTGCTGCTGCGAAGTTTT
TAAATACAACCGTCGCCCGGCGGAAACCAATCTGCGTCATACGTGTAAACGCATTATG
GATATGGTCAGCAACCAGCACCCGTGGTTCGGTATGGAACAAGAATATACCCTGATGG
GTACGGATGGCCATCCGTTTGGTTGGCCGAGCAATGGTTTCCCGGGTCCGCAGGGTCCG
TATTACTGCGGTGTCGGCGCAGATCGTGCTTACGGTCGCGACATTGTGGAAGCACACTA
TCGTGCTTGTCTGTACGCGGGTGTTAAAATCGCCGGCACCAATGCAGAAGTCATGCCG
GCTCAGTGGGAATTTCAAATTGGCCCGTGCGAAGGTATCAGCATGGGCGATCATCTGT
GGGTTGCTCGTTTCATCCTGCACCGCGTCTGTGAAGATTTTGGTGTGATTGCGACCTTC
GACCCGAAACCGATCCCGGGCAACTGGAATGGTGCTGGCTGCCATACCAACTTTAGCA
CGAAAGCGATGCGTGAAGAAAATGGCCTGAAATACATCGAAGAAGCAATCGAAAAAC
TGTCTAAACGTCATCAGTATCACATTCGCGCCTACGATCCGAAAGGCGGTCTGGACAA
CGCACGTCGCCTGACCGGTTTTCACGAAACGAGCAACATCAATGATTTCTCTGCGGGCG
TTGCCAATCGCTCAGCCTCGATTCGTATCCCGCGCACCGTCGGTCAAGAGAAAAAGG
CTATTTTGAAGATCGTCGCCCGAGTGCAAACTGTGACCCGTTCTCCGTGACGGAAGCCC
TGATCCGCACCTGTCTGCTGAATGAAACCGGCGATGAACCGTTCCAATACAAAAAT SEQ ID NO: 6 [Lactobacillus acidophilus strain 30SC GS]
>tr|F0TG87|F0TG87_LACA3 Glutamine synthetase OS = Lactobacillus acidophilus
(strain 30SC)
MSKQYTTEEIRKEVADKDVRFLRLCFTDINGTEKAVEVPTSQLDKVLTNDIRFDGSSIDGFV
RLEESDMVLYPDFSTWSVLPWGDEHGGKIGRLICSVHMTDGKPFAGDPRNNLKRVLGEM
KEAGFDTFDIGFEMEFHLFKLDENGNWTTEVPDHASYFDMTSDDEGARCRREIVETLEEIG
FEVEAAHHEVGDGQQEIDFRFDDALTTADRCQTFKMVARHIARKHGLFATFMAKPVEGQ
AGNGMHNNMSLFKNKHNVFYDKDGEPHLSNTALYFLNGILEHARAITAIGNPTVNSYKRLI
PGFEAPVYIAWAAKNRSPLVRIPSAGEINTRLEMRSADPTANPYLLLAACLTAGLKGIKEQK
MPMKPVEENIFEMTEEERAEHGIKPLPTTLHNAIKAFKEDDLIKSALGEHLTHSFIESKELEW
SKYSQSVSDWERQRYMNW SEQ ID NO: 7 [Zea Mays GS] (corn/Maize GS)
>tr|B4G1P1|B4G1P1_MAIZE Glutamine synthetase
MACLTDLVNLNLSDNTEKIIAEYIWIGGSGMDLRSKARTLSGPVTDPSKLPKWNYDGSSTG
QAPGEDSEVILYPQAIFKDPFRRGNNILVMCDCYTPAGEPIPTNKRYNAAKIFSSPEVAAEEP
WYGIEQEYTLLQKDTNWPLGWPIGGFPGPQGPYYCGIGAEKSFGRDIVDAHYKACLYAGI
NISGINGEVMPGQWEFQVGPSVGISSGDQVWVARYILERITEIAGVVVTFDPKPIPGDWNGA
GAHTNYSTESMRKEGGYEVIKAAIEKLKLRHREHIAAYGEGNERRLTGRHETADINTFSWG
VANRGASVRVGRETEQNGKGYFEDRRPASNMDPYVVTSMIAETTIIWKP

SEQ ID NO: 8
MGSSHHHHHHGGGGS

SEQ ID NO: 9
GSSHHHHHHGGGGS

SEQ ID NO: 10
HHHHHH
```

In addition to the foregoing, the same Sequence Listings are provided in computer readable form encoded in a file submitted herewith (SequenceListing_ST25_3FEB2023.txt; file size: 21,530 bytes; date of creation: Feb. 3, 2023) and herein incorporated by reference. The information recorded in computer readable form is identical to the written Sequence Listings provided herein, pursuant to 37 C.F.R. § 1.821(f).

The invention claimed is:

1. A composition comprising a fusion protein comprising i) glutamine synthetase protein (GS protein) and ii) at the N terminal end of the GS protein, a peptide comprising the sequence HHHHHH (SEQ ID NO: 10) (6×His) and a linker which is 2-10 amino acids, wherein the GS protein of i) is or comprises the protein of SEQ ID NO: 1, a variant thereof having glutamine synthetase enzyme activity and having at least 90% sequence identity to the sequence of SEQ ID NO: 1, or a variant thereof comprising SEQ ID NO: 1 except for the N terminal methionine at position 1 thereof and having glutamine synthetase activity; and a pharmaceutical excipient, wherein the composition is for use as a pharmaceutical formulated for systemic administration.

2. The pharmaceutical composition of claim 1, wherein the peptide comprises or consists of the sequence MGSSHHHHHHGGGGS (SEQ ID NO: 8) or GSSHHHHHHGGGGS (SEQ ID NO: 9).

3. The pharmaceutical composition of claim 1 wherein the GS protein is or comprises a protein of SEQ ID NO: 1, a variant thereof having glutamine synthetase enzyme activity and having at least 95% sequence identity to the sequence of SEQ ID NO: 1, or a variant thereof comprising a protein of SEQ ID NO: 1 except for an N terminal methionine at position 1 thereof and having glutamine synthetase enzyme activity.

4. The pharmaceutical composition of claim 1, wherein the fusion protein is conjugated to a polyethylene glycol (PEG).

5. The pharmaceutical composition of claim 1, wherein the peptide is conjugated to a PEG.

6. The pharmaceutical composition of claim 4, wherein the PEG is linked to the fusion protein at the N terminus.

7. The pharmaceutical composition of claim 5, wherein the PEG is linked to the fusion protein at the N terminus.

8. The pharmaceutical composition of claim 6, wherein the PEG is a 20 kDa N-terminal aldehyde PEG.

9. The pharmaceutical composition of claim 7, wherein the PEG is a 20 kDa N-terminal aldehyde PEG.

10. The pharmaceutical composition of claim 1, wherein the composition is in a form suitable for systemic non-oral administration to a mammalian subject.

11. The pharmaceutical composition of claim 1 wherein the fusion protein is in a form suitable for parenteral or subcutaneous administration to the subject.

12. The pharmaceutical composition of claim 1 wherein the fusion protein is provided as a preparation comprising multimeric forms of the protein or wherein the fusion protein is provided in monomeric form.

13. The pharmaceutical composition of claim 10, wherein the composition is in a form suitable for administration to a site other than muscle.

14. A pharmaceutical composition comprising:
a fusion protein comprising:
i) glutamine synthetase protein (GS protein) and
ii) at the N terminal end of the GS protein, a peptide comprising the sequence GGGGS (SEQ ID NO: 11),
wherein the GS protein of i) is or comprises the protein of SEQ ID NO: 1, a variant thereof having glutamine synthetase enzyme activity and having at least 90% sequence identity to the sequence of SEQ ID NO: 1, or a variant thereof comprising SEQ ID NO: 1 except for the N terminal methionine thereof at position 1 and having glutamine synthetase activity; and
a pharmaceutical excipient;
wherein the pharmaceutical composition is formulated for systemic administration.

15. A pharmaceutical composition according to claim 14 wherein the peptide further comprises the sequence HHHHHH (SEQ ID NO: 10).

16. The pharmaceutical composition of claim 1, further comprising an ammonia lowering agent.

17. A kit comprising the composition of claim 1 and an ammonia lowering agent.

* * * * *

```
                         SEQUENCE LISTING

<160> NUMBER OF SEQ ID NOS: 10

<210> SEQ ID NO 1
   <211> LENGTH: 373
   <212> TYPE: PRT
   <213> ORGANISM: Homo sapiens

<400> SEQUENCE: 1

Met Thr Thr Ser Ala Ser Ser His Leu Asn Lys Gly Ile Lys Gln Val
```

```
1               5                   10                  15
Tyr Met Ser Leu Pro Gln Gly Glu Lys Val Gln Ala Met Tyr Ile Trp
                20                  25                  30
Ile Asp Gly Thr Gly Glu Gly Leu Arg Cys Lys Thr Arg Thr Leu Asp
                35                  40                  45
Ser Glu Pro Lys Cys Val Glu Leu Pro Glu Trp Asn Phe Asp Gly
    50                  55                  60
Ser Ser Thr Leu Gln Ser Glu Gly Ser Asn Ser Asp Met Tyr Leu Val
65                  70                  75                  80
Pro Ala Ala Met Phe Arg Asp Pro Phe Arg Lys Asp Pro Asn Lys Leu
                85                  90                  95
Val Leu Cys Glu Val Phe Lys Tyr Asn Arg Arg Pro Ala Glu Thr Asn
                100                 105                 110
Leu Arg His Thr Cys Lys Arg Ile Met Asp Met Val Ser Asn Gln His
                115                 120                 125
Pro Trp Phe Gly Met Glu Gln Glu Tyr Thr Leu Met Gly Thr Asp Gly
                130                 135                 140
His Pro Phe Gly Trp Pro Ser Asn Gly Phe Pro Gly Pro Gln Gly Pro
145                 150                 155                 160
Tyr Tyr Cys Gly Val Gly Ala Asp Arg Ala Tyr Gly Arg Asp Ile Val
                165                 170                 175
Glu Ala His Tyr Arg Ala Cys Leu Tyr Ala Gly Val Lys Ile Ala Gly
                180                 185                 190
Thr Asn Ala Glu Val Met Pro Ala Gln Trp Glu Phe Gln Ile Gly Pro
                195                 200                 205
Cys Glu Gly Ile Ser Met Gly Asp His Leu Trp Val Ala Arg Phe Ile
210                 215                 220
Leu His Arg Val Cys Glu Asp Phe Gly Val Ile Ala Thr Phe Asp Pro
225                 230                 235                 240
Lys Pro Ile Pro Gly Asn Trp Asn Gly Ala Gly Cys His Thr Asn Phe
                245                 250                 255
Ser Thr Lys Ala Met Arg Glu Glu Asn Gly Leu Lys Tyr Ile Glu Glu
                260                 265                 270
Ala Ile Glu Lys Leu Ser Lys Arg His Gln Tyr His Ile Arg Ala Tyr
                275                 280                 285
Asp Pro Lys Gly Gly Leu Asp Asn Ala Arg Arg Leu Thr Gly Phe His
290                 295                 300
Glu Thr Ser Asn Ile Asn Asp Phe Ser Ala Gly Val Ala Asn Arg Ser
305                 310                 315                 320
Ala Ser Ile Arg Ile Pro Arg Thr Val Gly Gln Glu Lys Lys Gly Tyr
                325                 330                 335
Phe Glu Asp Arg Arg Pro Ser Ala Asn Cys Asp Pro Phe Ser Val Thr
                340                 345                 350
Glu Ala Leu Ile Arg Thr Cys Leu Leu Asn Glu Thr Gly Asp Glu Pro
                355                 360                 365
Phe Gln Tyr Lys Asn
    370

<210> SEQ ID NO 2
<211> LENGTH: 372
<212> TYPE: PRT
<213> ORGANISM: Homo sapiens

<400> SEQUENCE: 2
```

```
Thr Thr Ser Ala Ser Ser His Leu Asn Lys Gly Ile Lys Gln Val Tyr
 1               5                  10                 15

Met Ser Leu Pro Gln Gly Glu Lys Val Gln Ala Met Tyr Ile Trp Ile
                20                 25                 30

Asp Gly Thr Gly Glu Gly Leu Arg Cys Lys Thr Arg Thr Leu Asp Ser
            35                 40                 45

Glu Pro Lys Cys Val Glu Leu Pro Glu Trp Asn Phe Asp Gly Ser
 50                 55                 60

Ser Thr Leu Gln Ser Glu Gly Ser Asn Ser Asp Met Tyr Leu Val Pro
 65                 70                 75                 80

Ala Ala Met Phe Arg Asp Pro Phe Arg Lys Asp Pro Asn Lys Leu Val
                85                 90                 95

Leu Cys Glu Val Phe Lys Tyr Asn Arg Arg Pro Ala Glu Thr Asn Leu
                100                105                110

Arg His Thr Cys Lys Arg Ile Met Asp Met Val Ser Asn Gln His Pro
            115                120                125

Trp Phe Gly Met Glu Gln Glu Tyr Thr Leu Met Gly Thr Asp Gly His
            130                135                140

Pro Phe Gly Trp Pro Ser Asn Gly Phe Pro Gly Pro Gln Gly Pro Tyr
145                150                155                160

Tyr Cys Gly Val Gly Ala Asp Arg Ala Tyr Gly Arg Asp Ile Val Glu
                165                170                175

Ala His Tyr Arg Ala Cys Leu Tyr Ala Gly Val Lys Ile Ala Gly Thr
            180                185                190

Asn Ala Glu Val Met Pro Ala Gln Trp Glu Phe Gln Ile Gly Pro Cys
            195                200                205

Glu Gly Ile Ser Met Gly Asp His Leu Trp Val Ala Arg Phe Ile Leu
210                215                220

His Arg Val Cys Glu Asp Phe Gly Val Ile Ala Thr Phe Asp Pro Lys
225                230                235                240

Pro Ile Pro Gly Asn Trp Asn Gly Ala Gly Cys His Thr Asn Phe Ser
                245                250                255

Thr Lys Ala Met Arg Glu Glu Asn Gly Leu Lys Tyr Ile Glu Glu Ala
                260                265                270

Ile Glu Lys Leu Ser Lys Arg His Gln Tyr His Ile Arg Ala Tyr Asp
                275                280                285

Pro Lys Gly Gly Leu Asp Asn Ala Arg Arg Leu Thr Gly Phe His Glu
                290                295                300

Thr Ser Asn Ile Asn Asp Phe Ser Ala Gly Val Ala Asn Arg Ser Ala
305                310                315                320

Ser Ile Arg Ile Pro Arg Thr Val Gly Gln Glu Lys Lys Gly Tyr Phe
                325                330                335

Glu Asp Arg Arg Pro Ser Ala Asn Cys Asp Pro Phe Ser Val Thr Glu
                340                345                350

Ala Leu Ile Arg Thr Cys Leu Leu Asn Glu Thr Gly Asp Glu Pro Phe
                355                360                365

Gln Tyr Lys Asn
    370

<210> SEQ ID NO 3
<211> LENGTH: 1366
<212> TYPE: DNA
<213> ORGANISM: Homo sapiens

<400> SEQUENCE: 3
```

```
cgagagtggg agaagagcgg agcgtgtgag cagtactgcg gcctcctctc ctctcctaac      60
ctgctctcgc ggcctacctt tacccgcccg cctgctcggc gaccagaaca ccttccacca     120
tgaccacctc agcaagttcc cacttaaata aaggcatcaa gcaggtgtac atgtccctgc     180
ctcagggtga gaaagtccag gccatgtata tctggatcga tggtactgga gaaggactgc     240
gctgcaagac ccggaccctg gacagtgagc ccaagtgtgt ggaagagttg cctgagtgga     300
atttcgatgg ctccagtact ttacagtctg agggttccaa cagtgacatg tatctcgtgc     360
ctgctgccat gtttcgggac cccttccgta aggaccctaa caagctggtg ttatgtgaag     420
ttttcaagta caatcgaagg cctgcagaga ccaatttgag gcacacctgt aaacggataa     480
tggacatggt gagcaaccag caccccctggt ttggcatgga gcaggagtat accctcatgg     540
ggacagatgg gcaccccttt ggttggcctt ccaacggctt cccagggccc agggtccat      600
attactgtgg tgtgggagca gacagagcct atggcaggga catcgtggag gcccattacc     660
gggcctgctt gtatgctgga gtcaagattg cggggactaa tgccgaggtc atgcctgccc     720
agtgggaatt tcagattgga ccttgtgaag gaatcagcat gggagatcat ctctgggtgg     780
cccgtttcat cttgcatcgt gtgtgtgaag actttggagt gatagcaacc tttgatccta     840
agcccattcc tgggaactgg aatggtgcag gctgccatac caacttcagc accaaggcca     900
tgcgggagga gaatggtctg aagtacatcg aggaggccat tgagaaacta agcaagcggc     960
accagtacca catccgtgcc tatgatccca agggaggcct ggacaatgcc cgacgtctaa    1020
ctggattcca tgaaacctcc aacatcaacg acttttctgg tggtgtagcc aatcgtagcg    1080
ccagcatacg cattccccgg actgttggcc aggagaagaa gggttacttt gaagatcgtc    1140
gcccctctgc caactgcgac ccctttttcgg tgacagaagc cctcatccgc acgtgtcttc    1200
tcaatgaaac cggcgatgag cccttccagt acaaaaatta agtggactag acctccagct    1260
gttgagcccc tcctagttct tcatcccact ccaactcttc ccctctccc agttgtcccg     1320
attgtaactc aaagggtgga atatcaaggt cgttttttt cattcc                    1366
```

<210> SEQ ID NO 4
<211> LENGTH: 388
<212> TYPE: PRT
<213> ORGANISM: Artificial Sequence
<220> FEATURE:
<223> OTHER INFORMATION: Modified human GS protein

<400> SEQUENCE: 4

```
Met Gly Ser Ser His His His His His Gly Gly Gly Ser Met
1               5                   10                  15

Thr Thr Ser Ala Ser Ser His Leu Asn Lys Gly Ile Lys Gln Val Tyr
            20                  25                  30

Met Ser Leu Pro Gln Gly Glu Lys Val Gln Ala Met Tyr Ile Trp Ile
        35                  40                  45

Asp Gly Thr Gly Glu Gly Leu Arg Cys Lys Thr Arg Thr Leu Asp Ser
    50                  55                  60

Glu Pro Lys Cys Val Glu Glu Leu Pro Glu Trp Asn Phe Asp Gly Ser
65                  70                  75                  80

Ser Thr Leu Gln Ser Glu Gly Ser Asn Ser Asp Met Tyr Leu Val Pro
                85                  90                  95

Ala Ala Met Phe Arg Asp Pro Phe Arg Lys Asp Pro Asn Lys Leu Val
            100                 105                 110

Leu Cys Glu Val Phe Lys Tyr Asn Arg Arg Pro Ala Glu Thr Asn Leu
```

```
                115                 120                 125
Arg His Thr Cys Lys Arg Ile Met Asp Met Val Ser Asn Gln His Pro
            130                 135                 140
Trp Phe Gly Met Glu Gln Glu Tyr Thr Leu Met Gly Thr Asp Gly His
145                 150                 155                 160
Pro Phe Gly Trp Pro Ser Asn Gly Phe Pro Gly Pro Gln Gly Pro Tyr
                165                 170                 175
Tyr Cys Gly Val Gly Ala Asp Arg Ala Tyr Gly Arg Asp Ile Val Glu
            180                 185                 190
Ala His Tyr Arg Ala Cys Leu Tyr Ala Gly Val Lys Ile Ala Gly Thr
            195                 200                 205
Asn Ala Glu Val Met Pro Ala Gln Trp Glu Phe Gln Ile Gly Pro Cys
210                 215                 220
Glu Gly Ile Ser Met Gly Asp His Leu Trp Val Ala Arg Phe Ile Leu
225                 230                 235                 240
His Arg Val Cys Glu Asp Phe Gly Val Ile Ala Thr Phe Asp Pro Lys
                245                 250                 255
Pro Ile Pro Gly Asn Trp Asn Gly Ala Gly Cys His Thr Asn Phe Ser
            260                 265                 270
Thr Lys Ala Met Arg Glu Glu Asn Gly Leu Lys Tyr Ile Glu Glu Ala
            275                 280                 285
Ile Glu Lys Leu Ser Lys Arg His Gln Tyr His Ile Arg Ala Tyr Asp
290                 295                 300
Pro Lys Gly Gly Leu Asp Asn Ala Arg Arg Leu Thr Gly Phe His Glu
305                 310                 315                 320
Thr Ser Asn Ile Asn Asp Phe Ser Ala Gly Val Ala Asn Arg Ser Ala
                325                 330                 335
Ser Ile Arg Ile Pro Arg Thr Val Gly Gln Lys Lys Gly Tyr Phe
            340                 345                 350
Glu Asp Arg Arg Pro Ser Ala Asn Cys Asp Pro Phe Ser Val Thr Glu
            355                 360                 365
Ala Leu Ile Arg Thr Cys Leu Leu Asn Glu Thr Gly Asp Glu Pro Phe
370                 375                 380
Gln Tyr Lys Asn
385

<210> SEQ ID NO 5
<211> LENGTH: 1164
<212> TYPE: DNA
<213> ORGANISM: Artificial Sequence
<220> FEATURE:
<223> OTHER INFORMATION: pET30a+ vector, containing the gene for human
      GS

<400> SEQUENCE: 5
atgggcagca gccaccacca tcaccaccac ggcggcggcg gtagcatgac cacctcggca    60
agcagccacc tgaataaagg catcaaacag gtgtatatgt ctctgccgca gggtgaaaaa   120
gttcaagcca tgtacatttg atcgatggc accggtgaag gcctgcgttg caaaacccgc   180
acgctggact cagaaccgaa atgtgtggaa gaactgccgg aatggaactt tgatggtagc   240
tctacgctgc agtcggaagg cagtaattcc gacatgtatc tggttccggc ggccatgttt   300
cgtgatccgt tccgcaaaga cccgaacaaa ctggtgctgt gcgaagtttt taaatacaac   360 cgtcgccccgg cggaaaccaa tctgcgtcat acgtgtaaac gcattatgga tatggtcagc   420
aaccagcacc cgtggttcgg tatggaacaa gaatataccc tgatgggtac ggatggccat   480
```

```
ccgtttggtt ggccgagcaa tggtttcccg ggtccgcagg gtccgtatta ctgcggtgtc      540
ggcgcagatc gtgcttacgg tcgcgacatt gtggaagcac actatcgtgc ttgtctgtac      600
gcgggtgtta aaatcgccgg caccaatgca gaagtcatgc cggctcagtg gaatttcaa       660
attggcccgt gcgaaggtat cagcatgggc gatcatctgt ggggttgctcg tttcatcctg     720
caccgcgtct gtgaagattt tggtgtgatt gcgaccttcg acccgaaacc gatcccgggc      780
aactggaatg tgctggctg ccataccaac tttagcacga aagcgatgcg tgaagaaaat       840
ggcctgaaat acatcgaaga agcaatcgaa aaactgtcta acgtcatca gtatcacatt       900
cgcgcctacg atccgaaagg cggtctggac aacgcacgtc gcctgaccgg ttttcacgaa      960
acgagcaaca tcaatgattt ctctgcgggc gttgccaatc gctcagcctc gattcgtatc     1020
ccgcgcaccg tcggtcaaga gaaaaaaggc tattttgaag atcgtcgccc gagtgcaaac     1080
tgtgacccgt tctccgtgac ggaagccctg atccgcacct gtctgctgaa tgaaaccggc     1140
gatgaaccgt tccaatacaa aaat                                            1164

<210> SEQ ID NO 6
<211> LENGTH: 445
<212> TYPE: PRT
<213> ORGANISM: Lactobacillus acidophilus

<400> SEQUENCE: 6

Met Ser Lys Gln Tyr Thr Thr Glu Glu Ile Arg Lys Glu Val Ala Asp
1               5                   10                  15

Lys Asp Val Arg Phe Leu Arg Leu Cys Phe Thr Asp Ile Asn Gly Thr
            20                  25                  30

Glu Lys Ala Val Glu Val Pro Thr Ser Gln Leu Asp Lys Val Leu Thr
        35                  40                  45

Asn Asp Ile Arg Phe Asp Gly Ser Ser Ile Asp Gly Phe Val Arg Leu
    50                  55                  60

Glu Glu Ser Asp Met Val Leu Tyr Pro Asp Phe Ser Thr Trp Ser Val
65                  70                  75                  80

Leu Pro Trp Gly Asp Glu His Gly Gly Lys Ile Gly Arg Leu Ile Cys
                85                  90                  95

Ser Val His Met Thr Asp Gly Lys Pro Phe Ala Gly Asp Pro Arg Asn
            100                 105                 110

Asn Leu Lys Arg Val Leu Gly Glu Met Lys Glu Ala Gly Phe Asp Thr
        115                 120                 125

Phe Asp Ile Gly Phe Glu Met Glu Phe His Leu Phe Lys Leu Asp Glu
    130                 135                 140

Asn Gly Asn Trp Thr Thr Glu Val Pro Asp His Ala Ser Tyr Phe Asp
145                 150                 155                 160

Met Thr Ser Asp Asp Glu Gly Ala Arg Cys Arg Arg Glu Ile Val Glu
                165                 170                 175

Thr Leu Glu Glu Ile Gly Phe Glu Val Glu Ala His His Glu Val
            180                 185                 190

Gly Asp Gly Gln Gln Glu Ile Asp Phe Arg Phe Asp Asp Ala Leu Thr
        195                 200                 205

Thr Ala Asp Arg Cys Gln Thr Phe Lys Met Val Ala Arg His Ile Ala
    210                 215                 220

Arg Lys His Gly Leu Phe Ala Thr Phe Met Ala Lys Pro Val Glu Gly
225                 230                 235                 240

Gln Ala Gly Asn Gly Met His Asn Asn Met Ser Leu Phe Lys Asn Lys
```

-continued

```
                245                 250                 255
His Asn Val Phe Tyr Asp Lys Asp Gly Glu Phe His Leu Ser Asn Thr
            260                 265                 270

Ala Leu Tyr Phe Leu Asn Gly Ile Leu Glu His Ala Arg Ala Ile Thr
            275                 280                 285

Ala Ile Gly Asn Pro Thr Val Asn Ser Tyr Lys Arg Leu Ile Pro Gly
            290                 295                 300

Phe Glu Ala Pro Val Tyr Ile Ala Trp Ala Ala Lys Asn Arg Ser Pro
305                 310                 315                 320

Leu Val Arg Ile Pro Ser Ala Gly Glu Ile Asn Thr Arg Leu Glu Met
                325                 330                 335

Arg Ser Ala Asp Pro Thr Ala Asn Pro Tyr Leu Leu Ala Ala Cys
            340                 345                 350

Leu Thr Ala Gly Leu Lys Gly Ile Lys Glu Gln Lys Met Pro Met Lys
            355                 360                 365

Pro Val Glu Glu Asn Ile Phe Glu Met Thr Glu Glu Arg Ala Glu
            370                 375                 380

His Gly Ile Lys Pro Leu Pro Thr Thr Leu His Asn Ala Ile Lys Ala
385                 390                 395                 400

Phe Lys Glu Asp Asp Leu Ile Lys Ser Ala Leu Gly Glu His Leu Thr
                405                 410                 415

His Ser Phe Ile Glu Ser Lys Glu Leu Glu Trp Ser Lys Tyr Ser Gln
            420                 425                 430

Ser Val Ser Asp Trp Glu Arg Gln Arg Tyr Met Asn Trp
            435                 440                 445

<210> SEQ ID NO 7
<211> LENGTH: 356
<212> TYPE: PRT
<213> ORGANISM: Zea mays

<400> SEQUENCE: 7

Met Ala Cys Leu Thr Asp Leu Val Asn Leu Asn Leu Ser Asp Asn Thr
1               5                   10                  15

Glu Lys Ile Ile Ala Glu Tyr Ile Trp Ile Gly Gly Ser Gly Met Asp
                20                  25                  30

Leu Arg Ser Lys Ala Arg Thr Leu Ser Gly Pro Val Thr Asp Pro Ser
            35                  40                  45

Lys Leu Pro Lys Trp Asn Tyr Asp Gly Ser Ser Thr Gly Gln Ala Pro
50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Asn Ala Ala Lys
            100                 105                 110

Ile Phe Ser Ser Pro Glu Val Ala Glu Glu Pro Trp Tyr Gly Ile
            115                 120                 125

Glu Gln Glu Tyr Thr Leu Leu Gln Lys Asp Thr Asn Trp Pro Leu Gly
            130                 135                 140

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
                165                 170                 175
```

```
Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ser Gly Asp Gln Val Trp Val Ala Arg Tyr Ile Leu Glu Arg Ile
    210                 215                 220

Thr Glu Ile Ala Gly Val Val Thr Phe Asp Pro Lys Pro Ile Pro
225                 230                 235                 240

Gly Asp Trp Asn Gly Ala Gly Ala His Thr Asn Tyr Ser Thr Glu Ser
                245                 250                 255

Met Arg Lys Glu Gly Gly Tyr Glu Val Ile Lys Ala Ala Ile Glu Lys
            260                 265                 270

Leu Lys Leu Arg His Arg Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
            340                 345                 350

Ile Trp Lys Pro
        355

<210> SEQ ID NO 8
<211> LENGTH: 15
<212> TYPE: PRT
<213> ORGANISM: Artificial Sequence
<220> FEATURE:
<223> OTHER INFORMATION: Portion of modified human GS protein

<400> SEQUENCE: 8

Met Gly Ser Ser His His His His His His Gly Gly Gly Gly Ser
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Portion of modified human GS protein

<400> SEQUENCE: 9

Gly Ser Ser His His His His His His Gly Gly Gly Gly Ser
1               5                   10

<210> SEQ ID NO 10
<211> LENGTH: 6
<212> TYPE: PRT
<213> ORGANISM: Artificial Sequence
<220> FEATURE:
<223> OTHER INFORMATION: His tag peptide

<400> SEQUENCE: 10

His His His His His His
1               5
```